United States Patent
Uddin et al.

(10) Patent No.: US 11,730,398 B2
(45) Date of Patent: Aug. 22, 2023

(54) MOTION POWERED WEARABLE DEVICES AND USES THEREOF IN HEALTH MONITORING

(71) Applicant: The Board of Regents, The University of Texas System, Austin, TX (US)

(72) Inventors: Mohammed Jasim Uddin, Edinburg, TX (US); Aminur Rashid Chowdhury, Edinburg, TX (US); Ulises Vidaurri Romero, San Antonio, TX (US)

(73) Assignee: The Board of Regents, The University of Texas Syst, Austin, TX (US)

( * ) Notice: Subject to any disclaimer, the term of this patent is extended or adjusted under 35 U.S.C. 154(b) by 183 days.

(21) Appl. No.: 16/913,647

(22) Filed: Jun. 26, 2020

(65) Prior Publication Data
US 2021/0000388 A1 Jan. 7, 2021

Related U.S. Application Data

(60) Provisional application No. 62/870,966, filed on Jul. 5, 2019.

(51) Int. Cl.
*A61B 5/00* (2006.01)
*A61B 5/11* (2006.01)
(52) U.S. Cl.
CPC .......... *A61B 5/1113* (2013.01); *A61B 5/0022* (2013.01); *A61B 5/6801* (2013.01);
(Continued)

(58) Field of Classification Search
CPC .......... A61B 5/00; A61B 5/0022; A61B 5/08; A61B 5/11; A61B 5/1113; A61B 5/18;
(Continued)

(56) References Cited

U.S. PATENT DOCUMENTS 9,728,176 B2    8/2017   Keck et al.
10,105,108 B1 *   10/2018   Taptelis ................. G16H 80/00
(Continued)

OTHER PUBLICATIONS

NPL Search (May 13, 2022).*
(Continued)

*Primary Examiner* — Van T Trieu
(74) *Attorney, Agent, or Firm* — Dykema Gossett, PLLC; Denise L. Mayfield

(57) ABSTRACT

A health monitoring device is provided, and may be used in population health monitoring and disease tracing, as well as for individual subject health purposes. The health monitoring device comprises a triboelectric nanogenerator (TENG) for generating and storing electrical energy from mechanical activity of a user. The device provides a continuous and uninterrupted stream of physiological data received at a surface of the device in contact with a surface of the user. The triboelectric nanogenerator is a paper-based device comprising a paper-based material layer and a polydimethylsiloxane/polytetrafluoroethylene (PDMS/PTFE) material layer, each on a copper film. The device has enhanced sensitivity to motion, providing an improved device capable of converting small amounts of movement into electrical energy, and of recording and transmitting data of small physiological changes of a user to a receiver. The device is lithium free, and eliminates the necessity of recharging.

18 Claims, 13 Drawing Sheets

(52) U.S. Cl.
CPC ...... *A61B 5/742* (2013.01); *A61B 2560/0204* (2013.01); *A61B 2562/02* (2013.01)

(58) Field of Classification Search
CPC . A61B 5/202; A61N 1/00; A61N 1/04; H02N 1/00; H02N 1/04; H02N 1/0468; H02N 2/00; H02N 2/18
See application file for complete search history.

(56) References Cited

U.S. PATENT DOCUMENTS

| | | | |
|---|---|---|---|
| 11,101,747 B2 * | 8/2021 | Bae | H02N 1/04 |
| 11,114,955 B2 * | 9/2021 | Mallineni | H02J 50/40 |
| 2004/0154106 A1 | 8/2004 | Oles et al. | |
| 2006/0172641 A1 | 8/2006 | Hennige et al. | |
| 2009/0137169 A1 | 5/2009 | Nun et al. | |
| 2017/0196761 A1 * | 7/2017 | Hyde | A61M 16/026 |
| 2020/0316366 A1 * | 10/2020 | Wang | A61N 1/0492 |

OTHER PUBLICATIONS

Fischer, S.C.L., et al., "Bioinspired polydimethylsilozane-based composites with high shear resistance against wet tissue", Jrnl of the Mech Behavior of BioMed Materials 61 (2016), 87-95.

Fan, F-R., et al., "Transparent Triboelectric Nanogenerators and Self-Powered Pressure Sensors Based on Micropatterened Plastic Films", Nano Letters, American Chemical Society 12, 2109-3114 (2012), pubs.acs.org/NanoLett dx.doi.org/10/1021/nl300988z.

Yoon, H-J., et al., "Sustainable powering triboelectric nanogenerators: Approaches and the path towards efficient use", Nano Energy 51 (2018) 270-285.

Majeed, S., et al., "Pyrene-POSS nanohybrid as a dispersant for carbon nanotubes in solvents of various polarities: its synthesis and application in the preparation membrane", Nanoscale Research Letters (2012) 7:296.

Yang, Y., et al., "Liquid-Metal-Based Super-Stretchable and Structure-Designable Triboelectric Nanogenerator for Wearable Electronics", ACS Nano 12 (2018), 2027-2034.

Zhang, X-S., et al., "All-in-one self-powered flexible microsystems based on triboelectric nanogenerators", Nano Energy 47 (2018), 410-426.

Ruan, M., et al., "Preparation of PTFE/PDMS superhydrophobic coating and its anti-icing performance", RSC Advances 7 (2017), 41339.

Kim, Y.J., et al., "Effect of the relative permittivity of oxides on the performance of triboelectric nanogenerators", RSC Advances 7 (2017), 49368.

Weng., B., et al., "Fibrous cellulose membrane mass produced via forcespinning for lithium-ion battery separators", Cellulose 22 (2015), 1311-1320 DOI 10.1007/s10570-015-0564-8.

Wang, Z., "Triboelectric Nanogenerators as New Energy Technology for Self-Powered Systems and as Active Mechanical and Chemical Sensors", ACS Nano vol. 7, No. 11 (2013), 9533-9557.

Lee, B., et al., "The TriboElectric Effect Series", AlphaLab, Inc., https://www.alphalabinc.com/triboelectric-series/printout dated Jan. 22, 2022, copyright 2022 to AlphaLab, Inc.

Wang, Y., et al., "Triboelectric nanogenerators as flexible power sources", npj Flexible Electronics (2017) 1:10, doi: 10.1038/s41528-017-0007-8.

Pan, S., et al., "Fundamental Theories and basic principles of triboelectric effect: A review", Friction 7(a): 2-17 (2019).

Haghi, M., et al., "Wearable Devices in Medical Internet of Things: Scientific Research and Commercially Available Devices", Health c Inform Res. Jan. 2017, 23(1): 4-15.

Cuckler, G., et al., "National Health Expenditure Projections, 2017-26: Despite Uncertainty, Fundamentals Primarily Drive Spending Growth", Health Affairs 27, No. 3 (2018): 482-492.

Samsung Smartwatch Parts, iFixit, https://ifixit.com/Parts/Samsung_Smartwatch, printout dated Nov. 22, 2022, 7 pages.

Rathore, S., et al., "A Critical Review oon Triboelectric Nano generator", IOP Conf. Series: Materials Science and Engineering 377 (2018) 012186 doi:10.1088/1757-899x/377/1/012186.

Apple Watch Parts, iFixit, https://www.ifxit.com/Parts/Apple_Smartwatch, printout dated Nov. 22, 2022, 7 pages.

Apple Watch Series 4—Technical Specifications, https://support.apple.com/kb/SP778?locale=en_us, printout dated Nov. 22, 2022, 3 pages.

Sahin, H., et al., "A Study on Physical and Chemical Properties of Cellulose Paper Immersed in Various Solvent Mixtures", Int. J. Mol. Sci 2008, 9, 78-88.

Business Wire, Correcting and Replacing New Apple Watch has Lowest Ratio of Hardware Costs to Retail Price, IHS Teardown Reveals, Apr. 30, 2015, 5 pages, businesswire.com/news/home/20150430006412/en/Apple-Watch-Lowest-Ratio-Hardware-Costs-Retail.

MMT—Manufacture Modules Technologies, Smartwatch Smart. Swiss.Connected, https://mmt.ch/smartwatch/, printout dated Nov. 22, 2022, 9 pages.

Costa, M.N., et al., "A low cost, safe, disposable, rapid and self-sustainable paper-based platform for diagnostic testing: lab-on-paper", Nanotechnology 25 (2014) 094006, 14 pages.

Kang, M., et al., Recent Patient Health Monitoring Platforms Incorporating Internet of Things-Enabled Smart Devices, Int. Neurourol J 2018, 22 (Suppl 2): S76-82.

Forerunner 235 / Wearables / Garmin Malaysia, https://www.garmin.com.my/products/wearables/forerunner-235-blue/#specsTab, printout dated Nov. 22, 2022, 3 pages.

Traverse, C., et al., "Emergence of highly transparent photovoltaics for distributed applications", Nature Energy (2017), 13 pages, https://doi.org/10.1038/s41560-017-0016-9.

Ma, M., et al., "Development, applications, and future directions of triboelectric nanogenerators", Nano Research (2018), 11(6): 2951-2969.

Ma, M., et al., "Self-Recovering Triboelectric Nanogenerators as Active Multifunctional Sensors", Adv. Funct. Mater. 25 (2015), 6489-6494.

Wu, H., et al., "Energy Harvesters for Wearable and Stretchable Electronics: From Flexibility to Stretchability", Adv. Mater. 2016, www.MaterialsViews.com, 39 pages.

Ning, C., et al., "Washable textile-structured single-electrode triboelectric nanogenerator for self-powered wearable electronics", Jrnl. of Mat. Chem A (2018), 10 pages.

Chowdhury, S., et al., "Room temperature synthesis of polyvinyl alcohol stabilized palladium nanoparticles: Solvent effect on shape and electro-catalytic activity", Nano-Structures & Nano-Objects 14 (2018) 11-18.

Sun, D., et al., Korean J. Chem Eng (2013), 30(11), 2059-2067.

* cited by examiner

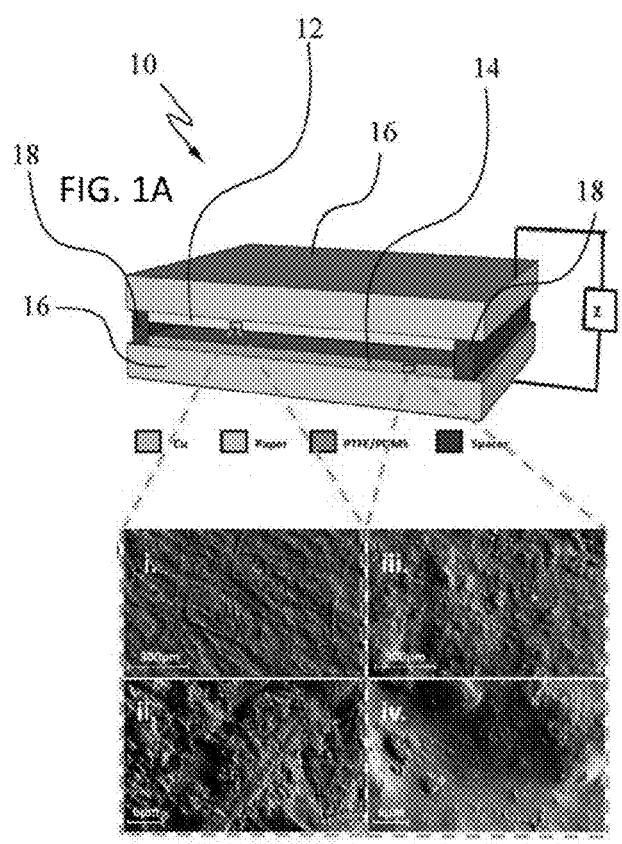
FIG. 1A
FIG. 1C
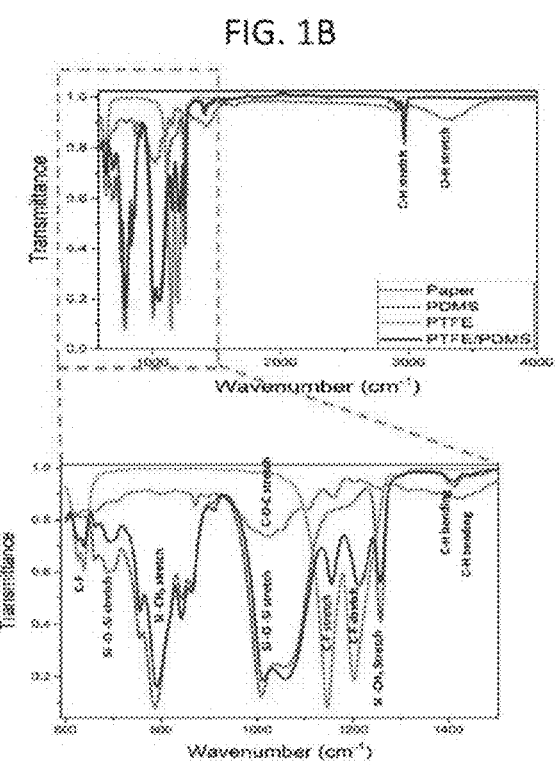
FIG. 1B
FIG. 1D

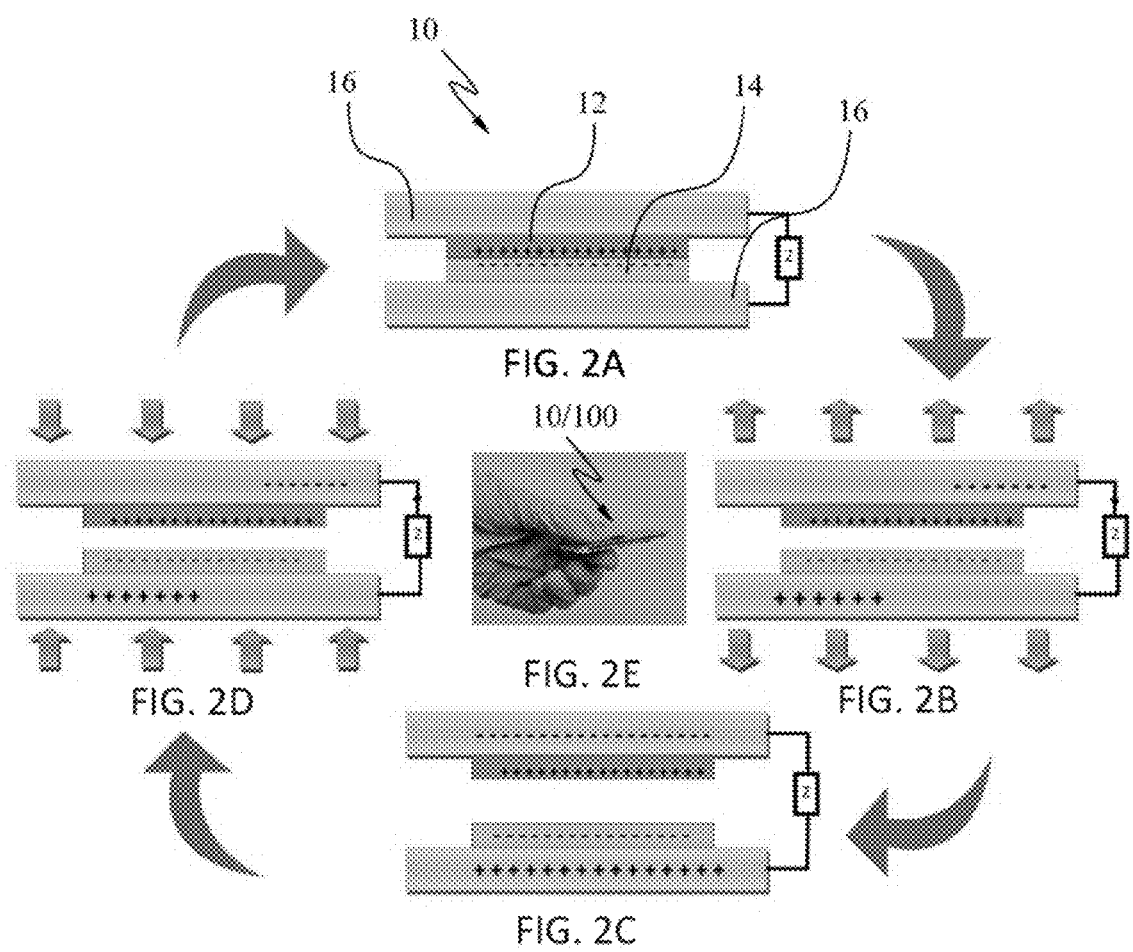

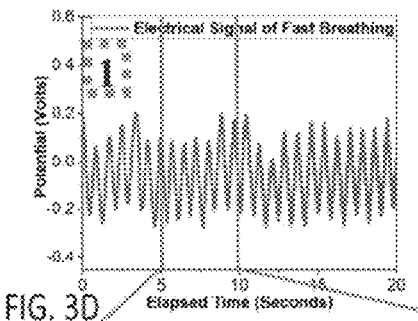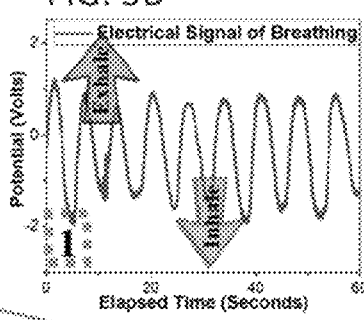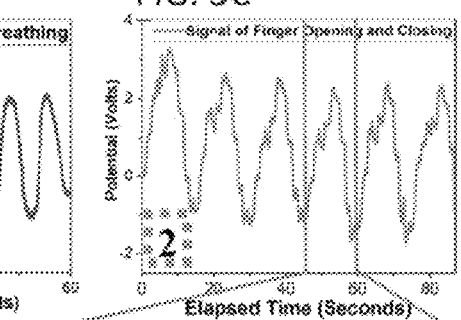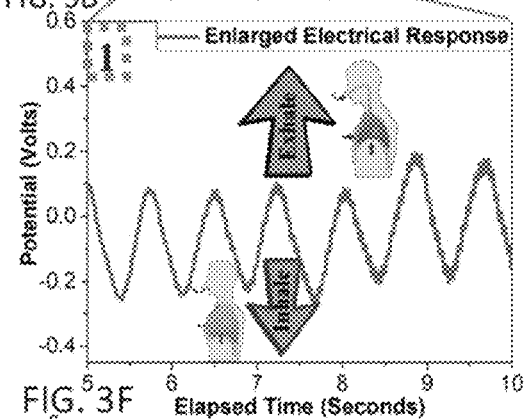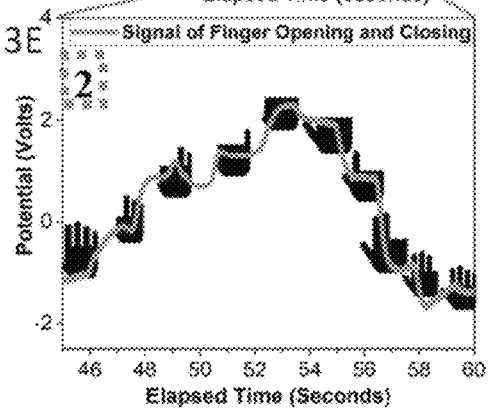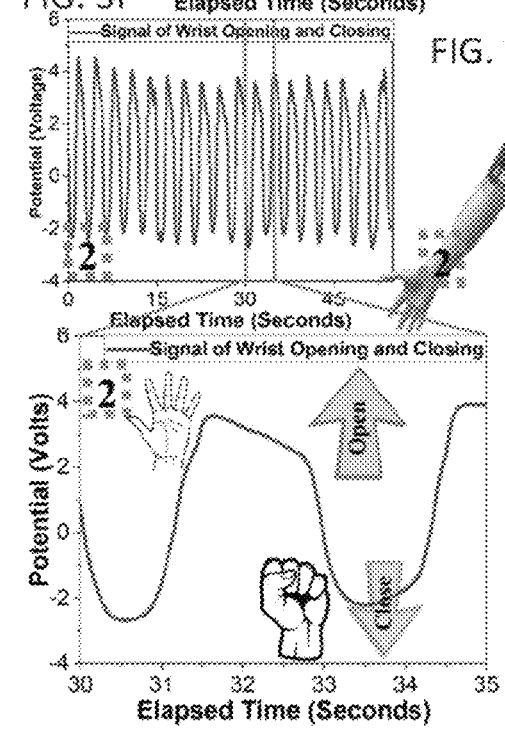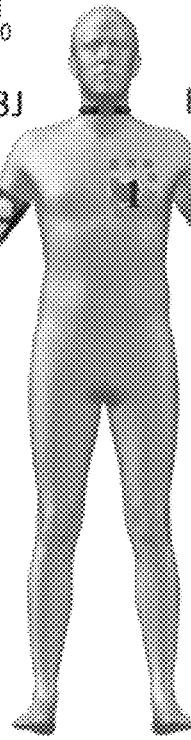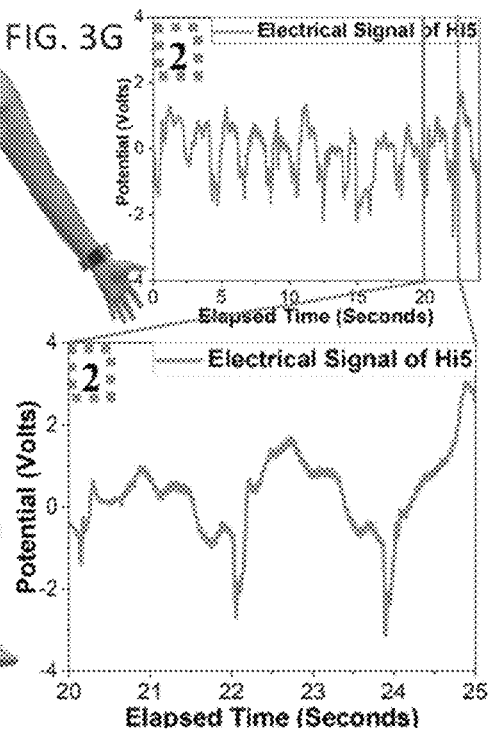

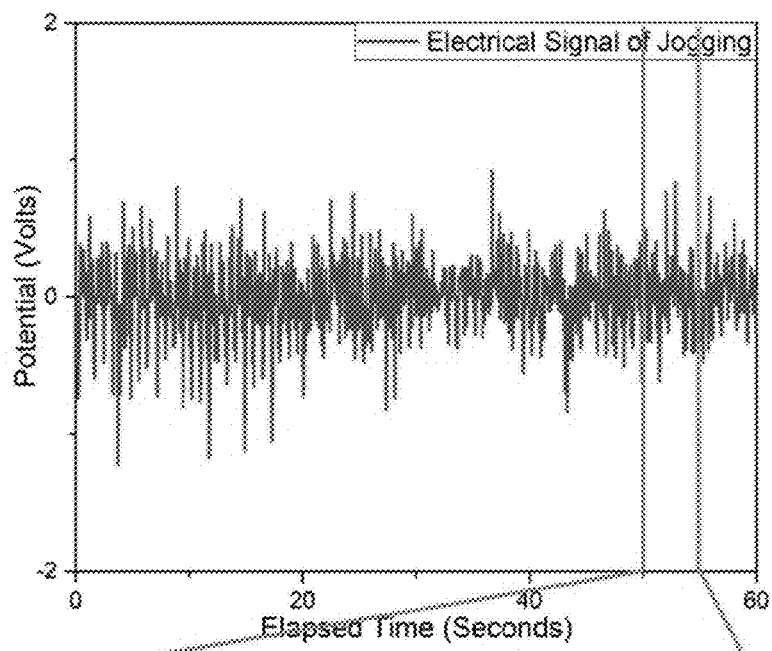
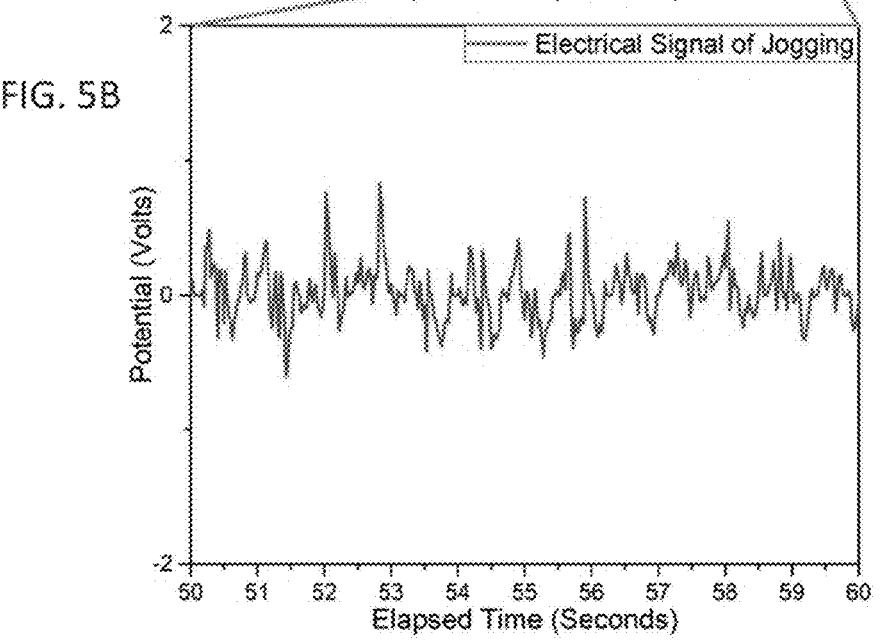
FIG. 5

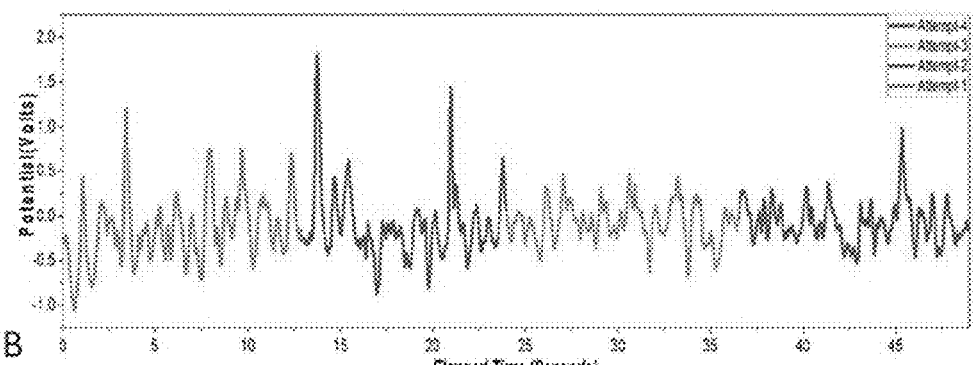
FIG. 7A
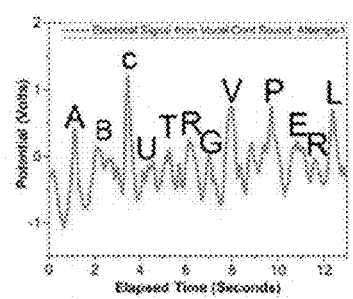
FIG. 7B
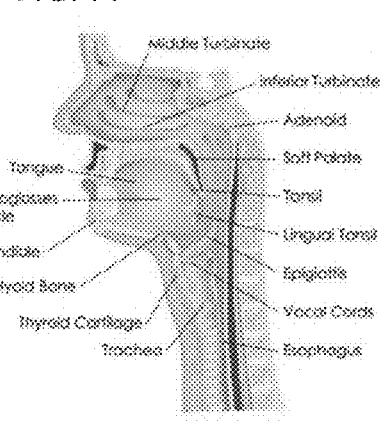
FIG. 7F
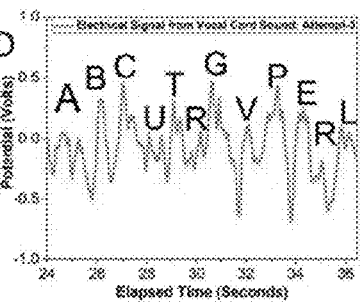
FIG. 7D
FIG. 7C
FIG. 7E
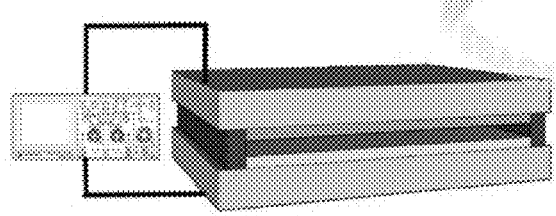
FIG. 7G
10/100
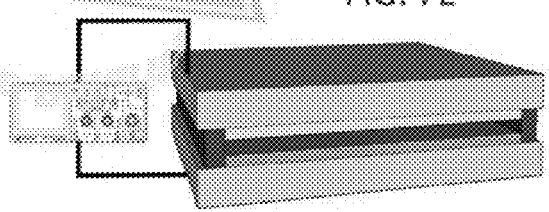
FIG. 7H
10/100

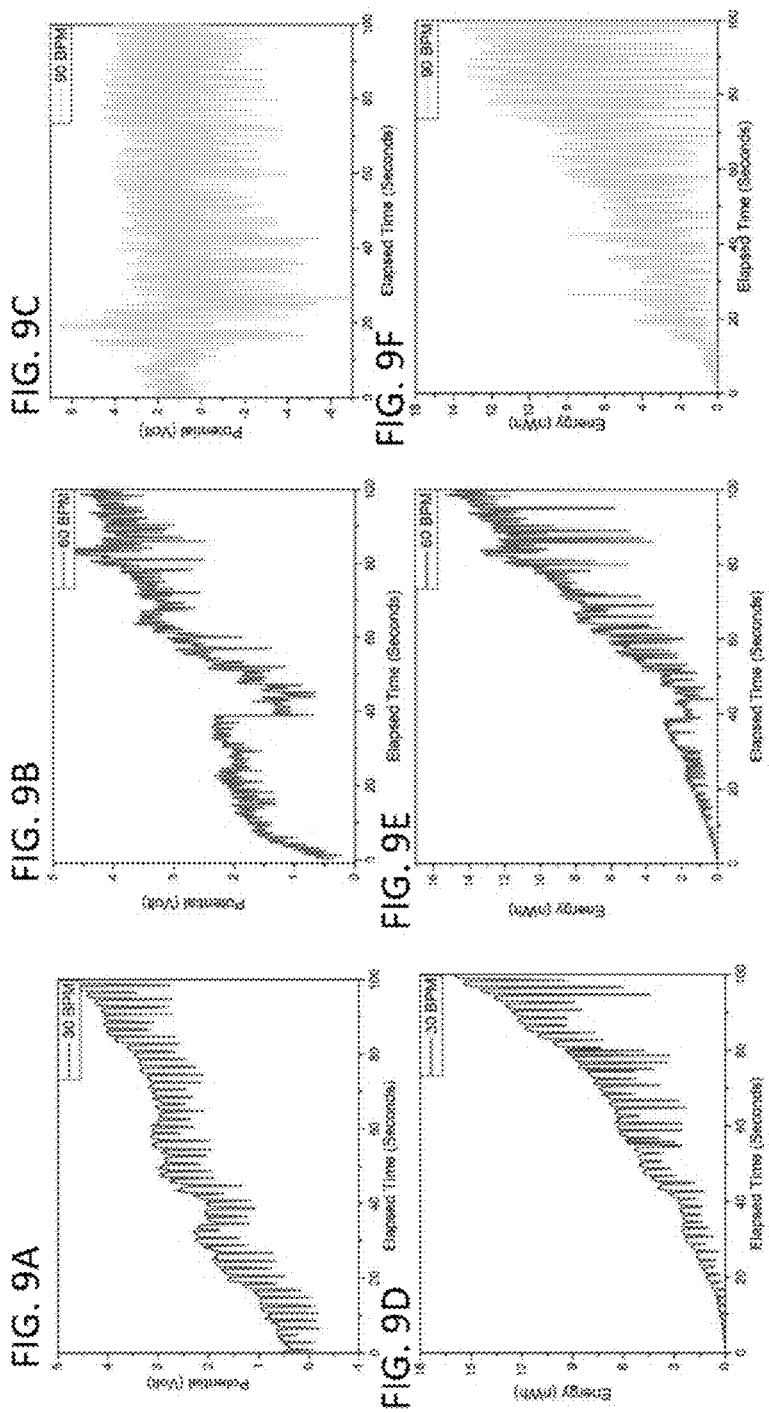

MOTION POWERED WEARABLE DEVICES AND USES THEREOF IN HEALTH MONITORING

This application claims priority to U.S. Provisional Patent Application 62/870,966 filed Jul. 5, 2019. The present disclosure relates generally to the field of battery free self-powered devices, and more particularly, to electric and/or kinetic motion powered health monitoring devices.

FIELD OF THE INVENTION

Background of the Invention

Triboelectric nanogenerators (TENGs) convert mechanical energy to electrical energy.[1] Many forms of mechanical energy, such as human movement, are not used to generate electrical energy, and hence this becomes an untapped source of energy, or "wasted" energy.

IoT-enabled (internet connected sources) devices have attracted the attention of healthcare professionals who seek to continuously track body movement[6]. The rapid population increase and the expanding cost of healthcare creates a need for improved methods and tools for monitoring health care[7]. This global need in the health care industry for modestly priced health care monitoring strategies remains unmet[8,9].

Commercially available health devices have an interrupted flow of incoming data, most are expensive, and require some type of manual data input. Additionally, these devices have sensors that lack a source of renewable and/or self-generating energy.

The TENG nanogenerator provides a tool to generate electrical energy by coupling a triboelectric effect and electrostatic induction to convert mechanical energy into electricity[1,11].

Battery powered wearable devices that include a lead-, nickel- and/or lithium-based battery, need periodic recharges to compensate for lost energy. A modern Li-ion battery only carries about 200 Wh/kg. Therefore, battery-operated wearable devices possess limitations that reduce the convenience and longevity of the device, and eventually require battery replacement. This creates added cost to the user, and limitations associated with long term use.

A need continues to exist for devices, particularly wearable devices that include a self-contained means for generating electricity and continuously transmitting that electrical energy to power the wearable device without interruption. Such a means would also preferably be capable of powering the device in a manner sufficient to support a continuous stream of data transfer from the wearable device, such as health and physiological data, to a wearer and/or a health care center, such as a hospital, assisted living facility, or municipal/government or central data collection agency. Such a device would also most preferably be capable of having an interne connection capacity, suitable for providing downloadable software into the device for various measurements and monitoring functions, such as for the measurement of physiological data through a wireless internet connection.

SUMMARY OF THE INVENTION

A battery-free, electrically powered wearable device, particularly a health monitoring device, is presented.

In some embodiments, the wearable device comprises a surface suitable for being in contact with a skin surface of a wearer, and a surface suitable for being in contact with an energy generating component comprising a triboelectric nanogenerator (TENG).

In some embodiments, the TENG comprises a paper, such as a cellulose paper, and Polydimethylsiloxane/Polytetrafluoroethylene (i.e., PDMS/PTFE) deposited on a copper film.

The device may be placed on virtually any skin surface of a wearer, such as the throat, chest, wrist, finger, foot, leg, arm, etc.

In another aspect, a method of monitoring physiological activity of a wearer is provided. In one embodiment, the method comprises contacting a skin surface of a wearer with a wearable device, the wearable device comprising triboelectric nanogenerator (TENG) configured to convert mechanical energy from body movements of the wearer to electrical energy to power the output of the wearable device. In one embodiment, the method further comprises receiving physiological data associated with the wearer through the TENG.

In yet another aspect, a method for identifying and tracking persons within a population having symptoms characteristic of a disease, especially a pandemic disease such as COVID-19, is provided. In this method, a person wearing the device described herein would be monitored for an identified physiological parameter, such as temperature and/or symptoms characteristic of an identified infection or disease. The data of these physiological parameters and/or disease symptoms would then be transferred to the wearable device in a continuous stream of data, and made available to the wearer. The stream of data may also be configured to be transferred to a population health data base, health epidemiological resource center, and/or a local health care provider network or institution (hospital, etc.). In this manner, a geographical pattern of disease spread and/or frequency of occurrence ("hot spot"), or of disease subsidence, may be identified immediately as the disease develops and/or subsides. This data collected and transmitted real-time in this manner may be employed to create governmental and other strategies for controlling disease spread and disease incidence in a population, as well as for planning and distributing health care resources. Because the wearable device is self-powered by virtue of the triboelectric nanogenerator (TENG), the method and monitoring devices present additional advantages in monitoring individuals in rural and/or underdeveloped geographical areas, where electricity and/or device re-charging resources may be limited and/or unavailable. It is envisioned that the methods and devices are particularly well suited for monitoring and/or controlling virtually any health threat within a population, for disease or pandemic, on a world-wide scale.

DESCRIPTION OF THE SEVERAL VIEWS OF THE DRAWING

FIG. 1A depicts a schematic diagram of a triboelectric nanogenerator (TENG) sensor device that may be utilized within a triboelectric universal health monitoring device (TUHMD) in accordance with an illustrative embodiment;

FIG. 1B depicts a Fourier transform infrared ray spectroscopy of a paper layer and Polytetrafluoroethylene (PTFE) a layer of a TENG device in accordance with an illustrative embodiment;

FIG. 1C depicts a scanning electron microscope (SEM) image of (i) paper, (ii) enlarged image of paper (iii) PTFE/Polydimethylsiloxane (PDMS) film, and (iv) enlarged image of PTFE/PDMS film for use in a TENG device in accordance with an illustrative embodiment;

FIG. 1D depicts an enlarged view on the Fourier transform infrared spectroscopy of the paper and PTFE layers of a TENG device in accordance with an illustrative embodiment;

FIG. 2A depicts a paper layer and a PTFE/PDMS layer of a TENG device in full contact mode due to the application of an external load in accordance with an illustrative embodiment;

FIG. 2B depicts a paper layer and a PTFE/PDMS layer of a TENG device in release mode due to the release of the external load in accordance with an illustrative embodiment;

FIG. 2C depicts a paper layer and a PTFE/PDMS layer of a TENG device in full separation mode in accordance with an illustrative embodiment;

FIG. 2D depicts a paper layer and a PTFE/PDMS layer of a TENG device under load mode in accordance with an illustrative embodiment;

FIG. 2E depicts an optical image of a TENG device configured for use in a triboelectric universal health monitoring device (TUHMD) in accordance with an illustrative embodiment;

FIG. 3A depicts an electrical signal of a fast breathing individual from a TUHMD device having a TENG device therein and being placed on the chest of the individual of in accordance with an illustrative embodiment;

FIG. 3B depicts an electrical signal of a normal breathing individual from a TUHMD device having a TENG device therein and being placed on the chest of the individual in accordance with an illustrative embodiment;

FIG. 3C depicts an electrical signal of a finger opening and closing from a TUHMD device having a TENG device therein and being placed on a wrist of an individual in accordance with an illustrative embodiment;

FIG. 3D depicts an enlarged view of an electrical signal of a fast breathing (inhale and exhale) individual from a TUHMD device having a TENG device therein and being placed on the chest of the individual in accordance with an illustrative embodiment;

FIG. 3E depicts an enlarged view of the electrical signal of finger opening and closing of FIG. 3C in accordance with an illustrative embodiment;

FIG. 3F depicts an electrical signal of wrist opening and closing from a TUHMD device having a TENG device therein and placed in the wrist of an individual in accordance with an illustrative embodiment;

FIG. 3G depicts an electrical signal of a "High 5" from a TUHMD device having a TENG device therein and placed in the wrist of an individual in accordance with an illustrative embodiment;

FIG. 3H depicts an enlarged view of the electrical signal of FIG. 3H in accordance with an illustrative embodiment;

FIG. 3I depicts an enlarged view of the electrical signal of FIG. 3G in accordance with an illustrative embodiment;

FIG. 3J depicts different positions on the human body under test in accordance with an illustrative embodiment;

FIG. 5A depicts an electrical signal of jogging movement from a TUHMD device having a TENG device therein and placed in the wrist of an individual in accordance with an illustrative embodiment;

FIG. 5B depicts an enlarged view of the electrical signal of FIG. 5A in accordance with an illustrative embodiment;

FIG. 7A depicts an electrical response of four attempts of an individual to pronounce the letters A, B, C, U, T, R G, V, P E, R, L from a TUHMD device having a TENG device therein and placed on the vocal cord of the individual in accordance with an illustrative embodiment;

FIG. 7B depicts an enlarged view of the electrical signal from a first attempt at pronouncing the letters in accordance with an illustrative embodiment;

FIG. 7C depicts an enlarged view of the electrical signal from a second attempt at pronouncing the letters in accordance with an illustrative embodiment;

FIG. 7D depicts an enlarged view of the electrical signal from a third attempt at pronouncing the letters in accordance with an illustrative embodiment;

FIG. 7E depicts an enlarged view of the electrical signal from a fourth attempt at pronouncing the letters in accordance with an illustrative embodiment;

FIG. 7F is a schematic representation of the vocal system of a human body in accordance with an illustrative embodiment;

FIG. 7G depicts an electrode connection status in the first and second attempts (see FIGS. 7B and 7C) in accordance with an illustrative embodiment;

FIG. 7H depicts an electrode connection status in the third and fourth attempts (see FIGS. 7D and 7E) in accordance with an illustrative embodiment;

FIG. 9A depicts a voltage response of a TUHMD device having a TENG device therein in 30 BPM over 100 seconds of elapsed time in accordance with an illustrative embodiment;

FIG. 9B depicts a voltage response of a TUHMD device having a TENG device therein in 60 BPM over 100 seconds of elapsed time in accordance with an illustrative embodiment;

FIG. 9C depicts a voltage response of a TUHMD device having a TENG device therein in 90 BPM over 100 seconds of elapsed time in accordance with an illustrative embodiment;

FIG. 9D depicts an energy response of a TUHMD device having a TENG device therein in 30 BPM over 100 seconds of elapsed time in accordance with an illustrative embodiment;

FIG. 9E depicts an energy response of a TUHMD device having a TENG device therein in 60 BPM over 100 seconds of elapsed time in accordance with an illustrative embodiment;

FIG. 9F depicts an energy response of a TUHMD device having a TENG device therein in 90 BPM over 100 seconds of elapsed time in accordance with an illustrative embodiment;

DETAILED DESCRIPTION OF THE INVENTION

Figure 4A:
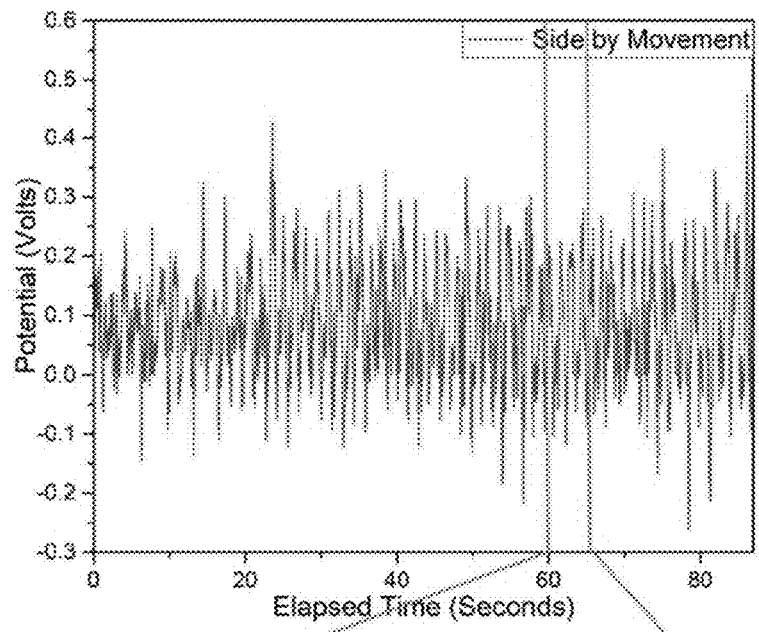
FIG. 4A depicts an electrical signal of side-by-side movement from a TUHMD device having a TENG device therein and placed in the wrist of an individual in accordance with an illustrative embodiment.

Triboelectric nanogenerator (TENG) devices use the coupling of triboelectric effect and electrostatic induction to harvest the multifarious forms of mechanical energy to convert them into electricity. Depending on material selection in the triboelectric series, TENGs create static polarized charges to various degrees upon an external force applied onto the layers. When the two triboelectric materials contact, induced charges flow between the two conductive electrodes, leading to opposite static charge acquisition on the surface. As the two layers then separate, the layer with larger electronegativity partakes charge, while the less electronegative layer becomes charge depleted. This charge transformation between the two electrodes offsets potential difference to create an output of electrical signals. In application, the relative motion causes this induction of charges. Since mechanical, also termed "wasted" energy, is already present in human activity, these nanogenerators transform the kinetic energy of movement into electrical electric energy, and channel this electrical energy into various applications suitable for use in wearable and other types of devices. In this way, the present invention in accordance to one embodiment is directed to a TENG device that can bio harvests mechanical energy to perform self-powered motion sensor for wearable and other types of devices.

One aspect of the present invention is directed generally to a TENG device 10 that can be incorporated into any suitable type of wearable device and utilized as a power source by transforming the kinetic energy from the user's body movements into electrical energy for the wearable device. FIG. 1 and FIG. 2 provide a schematic representation of TENG device 10 in accordance with one embodiment of the present invention. According to one embodiment, TENG device is incorporated within a wearable device, such as for example, a triboelectric universal health monitoring device (TUHMD) 100 as described in a greater detail below (see FIG. 6). According to one embodiment as shown in FIG. 1 and FIG. 2, TENG device 10 may comprise a paper-based TENG that includes a paper or fibrous material layer 12 and a polymer material layer 14, each provided on a conductive film layer 16 (such as for example a copper film). Depending on the particular embodiment, the paper material layer 12 may comprise any suitable paper-based material, fibrous material, cellulose type material or the like. The polymer material layer 14 may comprise any suitable polymer or combination of polymer materials depending on the particular embodiment. As non-limiting examples, polymer material layer 14 may comprise Polydimethylsiloxane (PDMS), Polytetrafluoroethylene (PTFE), or a combination of PDMS/PTFE. It is also recognized that and other suitable polymer materials may be utilized for layer 14.

TENG device 10 may be configured to adapt a vertical contact-separation mode, which generates power based on recurrent conversion between contact and separation. In such and embodiment, as device 10 is mechanically triggered (such as by movement of the human body), an electric output signal is generated from the transformed energy of the movement. The configuration of the vertical contact-separation mode can enable TENG device 10 to be particularly suitable for harvesting periodic motion and vibration (e.g., everyday real movement).

Figure 4B:
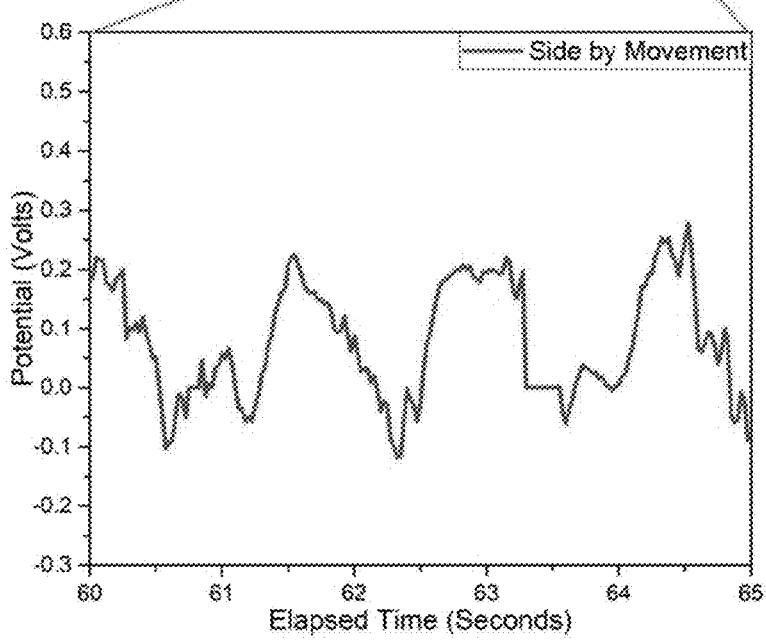
FIG. 4B depicts an enlarged view of the electrical signal of FIG. 4A in accordance with an illustrative embodiment.

In one embodiment, TENG device 10 was configured with a paper material layer 12 and a Polydimethylsiloxane (PDMS)/Polytetrafluoroethylene (PTFE) layer 14 and then evaluated on three different parameters: respiration, motion, vocal cord and vibratory energy levels. For respiration, fast and normal breathings were tested. The second parameter consisted of 30, 60, and 90 beats per minute frequencies for applied stresses. Wrist opening and closing, signaling of finger opening and closing as well as more casual body motions such as handshake and hi-five were also tested for TENG device 10 according to this embodiment. Lastly, spoken letters "A, B, C, U, T, R, G, V, P, E, R, L" for vibration recognition of vocal cords was assessed. Thorough characterization of the composite was attained by Fourier-transform infrared spectroscopy (FTIR) and SEM. TENG device 10 of the present invention provided an exceptional response to the stimuli and test evaluations described above, as illustrated in greater detail in FIG. 3 and FIG. 4.

TENG device 10 of the present invention can also be easily fabricated using the paper layer 12 and polymer layer 14 described above according to one embodiment. As a result, TENG device 10 could be suitable for use as a TENG sensor within a wearable medical device to produce a triboelectric universal health monitoring device (TUHMD) 100 as described in greater detail and shown schematically (see FIG. 6) herein.

In accordance with one embodiment, the engineered TENG device 10 of the present invention demonstrated acute sensitivity to motion and vibration to propagate electrical signals. Due to this demonstrated sensitivity and in light of the established data communication between motion and the device 10, device 10 may be particularly useful in a TUHMD device and system 100 for use in the healthcare industry where there is an increasing demand for continuous auditing of physiological movements.

According to another aspect and embodiment of the present invention, the TENG device 10 described herein may be utilized in a watch or similar wearable device 100 (which may or may not be intended for use has a healthcare-related device) as an energy source. The use of TENG device 10 of the present invention in a smartwatch or similar device 100 could provide an effective means to replace and eliminate the typical external power sources currently utilized in conventional smartwatches. Instead, the TENG device 10 of the present invention based energy generating capacity would power the watch device 100 as the TENG device 10 as it is mechanically triggered, hence reducing and/or eliminating the need for an external power source.

According to another aspect and embodiment of the present invention, the TENG device 10 may be utilized in connection with small-scale electronics 100 as a power generating source. Such TENG device 10 may comprise a paper-based TENG with Polydimethylsiloxane (PDMS)/Polytetrafluoroethylene (PTFE) on copper film as described above and replace traditional external power sources commonly utilized for electronics.

Turning now to the several figures, and in particular FIG. 1, TENG device 10 configured for use in connection with a TUHMD device 100 is shown in accordance with one embodiment. As shown in FIG. 1A, TUHMD device 100 may be fabricated with a TENG 10 comprising paper and PTFE/PDMS copolymer composites due to their positions in the triboelectric series, relative availability and cost efficiency. As shown in FIG. 1A, according to one embodiment, TUHMD device 100 may include a TENG component 10 comprising a paper material layer 12 having a copper film 16 disposed on its exterior side and a PTFE and/or PDMS material layer 14 also having a copper film 16 disposed on its exterior. As further shown in FIG. 1A, the two layers 12 and 14 may be spaced apart from one another by a spacer component 18 provided on each end of the TENG component 10. The difference in the triboelectric series of paper and PTFE layers 12 and 14 can denote good triboelectric effect between the materials. In addition, the appplication of PDMS with PTFE for synthesizing PTFE/PDMS composite can provide higher mechanical strength, better electrical conductivity, and durability for TENG 10 and TUHMD 100. The copper films 16 (which can alternatively comprise and suitable conductive material) for each of the triboelectric layers 12 and 14 enable the layers to operate as electrodes.

FIG. 1B provides a schematic representation of a Fourier Transform Infrared (FTIR) spectrum of TENG component 10 comprising a paper material layer 12 and PTFE/PDMS material layer 14 according to one embodiment. As further shown in FIG. 1B, FTIR data is also shown schematically for embodiments where polymer layer 14 of TENG component 10 comprises only PTFE and only PDMS for comparison purposes.

FIG. 1C provides a schematic representation of a scanning electron microscope (SEM) rendition of an observed surface morphology of the paper material layer 12 and polymer material layer 14 (comprising PTFE/PDMS) according to one embodiment. In the shown embodiment, the paper layer 12 was gold-sputtered before imaging at SEM. The sample for paper layer 12 was observed at 1000V and 1500V of Electron High Tension (EHT) voltage as depicted in FIG. 1C(i) and FIG. 1C(ii). As shown, the fiber structure of the cellulose fiber from the paper layer 12 is clearly evident in the SEM image. This fiber structure results in higher roughness and higher area of the surface of the paper layer 12 (see FIG. 1C(i) and FIG. 1C(ii)).

On the other hand, FIG. 1C(iii) and FIG. 1C(iv) reflect the image taken by SEM at 1300V EHT to observe the surface morphology of PTFE/PDMS composite material layer 14. Generally, pure PDMS shows smooth surface under SEM. However, according to the embodiment depicted, as PTFE is used for the formation co-polymer composite, the roughness of the surface rises. These grain types structure in the surface clearly point out the roughness of PTFE/PDMS copolymer layer 14 surface. The higher the amount of PTFE, the higher the amount of roughness, and accordingly, it is recognized that the surface roughness for the copolymer layer 14 may be advantageously modified based on the ratio of PTFE and PDMS materials.

FIG. 1D provides a schematic representation of an enlarged view of the FTIR spectrum shown in FIG. 1B from 600 to 1500 $cm^{-1}$ according to one embodiment of the present invention. As shown in FIG. 1D, according to the embodiment of TUHMD 100 and TENG 10 as described with reference to FIG. 1, two sharp peaks can be observed at 790 $cm^{-1}$ and 1255 $cm^{-1}$ which points the presence of Si—$CH_3$ from the PDMS of PDMS/PTFE composites of polymer layer 14. As shown, the peaks at 690 $cm^{-1}$ and 1015 $cm^{-1}$ mark the stretching of the Si—O—Si bond of PDMS of PDMS/PTFE composites of layer 14. The FTIR spectrum from embodiments where layer 14 comprised pure PDMS exhibited similar peaks like the PDMS of the composite layer 14. Furthermore, the two strong symmetric peaks at 1155 $cm^{-1}$ and 1213 $cm^{-1}$ correspond the C—F stretching of PTFE. These peaks are quite similar like the symmetric peaks of pure PTFE. C—H stretches from PDMS is responsible for the sharp peak at 1411 $cm^{-1}$ and 2958 $cm^{-1}$. The spectrums are clear evidence of the presence of PTFE and PDMS in the composite layer 14. These FTIR graphs demonstrate the coexistence of PTFE and PDMS on copolymer state when used in layer 14. Both PTFE and PDMS retain their chemical characteristics while being on the same composite surface. On the other hand, the FTIR spectrum from the paper of layer 12 shows a wide peak at 1022 $cm^{-1}$ which is due to the vibration of C—O—C bond in the Cellulose structure. As further shown in FIG. 1D, the peaks at 1425 $cm^{-1}$ and 3313 $cm^{-1}$ are representing the presence of C—H bending and O—H stretching respectively in the Cellulose. As paper used in layer 12 is produced from Cellulose fibers, it is expected that the FTIR spectrum of the paper will show the characteristics of Cellulose. These peaks clarify the presence of Cellulose from the paper in layer 12.

As described herein, the TUHMD device 100 and TENG 10 therein may operate due to the contact triboelectrification and electrostatic induction between paper and PTFE/PDMS material layers 12 and 14, respectively. According to one embodiment, TUHMD 100 may function as a Vertical mode Triboelectric Nanogenerator. FIG. 2 provides a schematic representation of the triboelectrification process in accordance with one embodiment of the present invention. Whenever an external load is applied on the TUHMD device 100, the Paper and PTFE/PDMS material layers 12 and 14 may initiate coming to close at each other. Eventually, both layers 12 and 14 get fully contacted with each other (see FIG. 2A). When they are in full contact as shown in FIG. 2A, transient surface polarization is generated and triboelectrification occurs. According to the triboelectric series, the paper in layer 12 holds a higher position than the PTFE in layer 14 as electropositive materials. As a result, the paper in layer 12 will supply electrons while the PTFE/PDMS composite in layer 14 will receive electrons at the surface.

According to this embodiment, when external pressure is released from the TUHMD device 100 (and TENG component 10), the layers 12 and 14 start moving far from each other and the transient surface polarization is broken (see FIG. 2B). This separation results in the higher electric potential at the paper in layer 12 connected to copper (Cu) electrode in film 16. The electrons start flowing along the circuit to recompense the triboelectric charges and maintain electrical equilibrium in the device 100/10. An output voltage and current signal can be clearly detected due to this electrostatic induction. Once the external load is fully released there will be no electron flow within the circuit (see FIG. 2C). Due to the flow of the electrons from the PTFE/PDMS (in layer 14) connected electrode to the paper (in layer 12) connected electrode at the previous step, the electrodes at this stage reach a situation where they have the same electric potential. When external pressure is applied on the device 100/10 again, the triboelectric layers 12 and 14 start moving close to each other (see FIG. 2D). The electric potential of the electrodes of the paper (in layer 12) becomes lower than that of the other electrodes (in layer 14). Accordingly, electrons start to move in the opposite direction of the releasing stage and induce the positive charges of the electrodes of PTFE/PDMS generating a reversed voltage output and current signal. Eventually, the triboelectric layers are in full contact again, as shown in FIG. 2A. The electricity generation from TUHMD 100 by external force or load can be summed in a cyclic pattern as illustrated through the process depicted in FIG. 2 overall. The pressure can be applied from one or both sides of the TENG 10 of TUHMD 100 (e.g., layers 12 and 14) to initiate triboelectric effect. FIG. 2E shows the optical view of finger pressing on the TENG 10 of TUHMD 100 on both sides, as an illustration of this applied pressure.

FIG. 3 provides several schematic representations of performance data for TUHMD 100 and TENG 10 in accordance with one embodiment of the present invention. To comprehensively investigate the real-life performance of the fabricated nanogenerator (TENG 10) as body movement sensor, the nanogenerator (TENG 10) was tested with different body motions by attaching the nanogenerator (TENG 10) on different body locations (point 1 and point 2) as best shown in FIG. 3J. The electrical signal of nanogenerator (TENG 10) while attached in point 1 (Chest) is demonstrated in FIG. 3A and FIG. 3B.

FIG. 3A describes the response of nanogenerator (TENG 10) under athletic breathing conditions. As shown, this response was generated by fast breathing (inhaling an exhaling) of the subject causing expansion and contraction of the rib cage. An enlarged view of the response of the athletic breathing individual is depicted in FIG. 3D, which demonstrates harmonized responses. However, the ups and downs in FIG. 3D are due to real-life body motion vibrations and spring actions as well as cantilever movement of the nanogenerator (TENG 10). The polarity of the response depends on the electrode connection. Inhalation and exhalation follow the working mechanism of TENG 10 (between layers 12 and 14) as previously described with reference to FIG. 2A-FIG. 2D. Inhalation brings the two opposite triboelectric material layers 12 and 14 closer to each other as nanogenerator (TENG 10) is pushed outward while the holding tape holds the device 100 (incorporating TENG 10) back. This can initiate triboelectric action as opposite charges accumulate to the inward portions of triboelectric the material layers 12 and 14 of paper (12) and PTFE/PDMS (14) because of the layers 12 and 14 getting closer to each other. This is followed by the flow of electrons from one electrode layer 12/14 to another electrode layer 12/14 through a connected circuit.

Similar but opposite action can be triggered by exhalation and inward movement of the rib cage. As the triboelectric layers 12 and 14 get far away from each other through relaxation of the human body parts as well as relaxation of the device, the triboelectric material layers 12 and 14 start acting in the opposite way by charge transfer to compensate the relaxation. This reverse action generates exactly the opposite potential compared to the inhalation and outward movement of the rib cage as depicted in FIGS. 3A, 3B and 3D.

FIGS. 3B and 3D illustrate that fast breathing generates small vibratory response compared to slow breathing, which may make TENG device 10 (and TUHMD 100) of the present invention better suited for understanding athletic or regular motion as well as inhalation or exhalation. During testing of TENG device 10 according to one embodiment, it was demonstrated that fast breathing generated electricity with nearly 0.4V (−0.2V to +0.2V) of range. It was also demonstrated this range goes 10 times larger during regular breathing (−2V to +2V). Throughout slow/regular breathing, the TENG device 10 got enough time to get back to original position after every stretching hence the response is smooth voltage that is larger due to the ability to retain full capacity during the whole working cycle (as illustrated in FIG. 2).

During fast rib cage movement, the two triboelectric layers 12 and 14 had lesser time to release the charge and get back to the original state hence it did not generate higher voltage comparable to the slow breathing. The TENG device 10 according to one embodiment was also tested with side by side movement (see FIG. 4) and jogging movement (see FIG. 5) while being attached to the chest (position 1 as shown in FIG. 3J). Both movements show symmetrical response though jogging response that is more abrupt looking due to dynamic movement. However, this response is largely symmetrical in shape rather than peak value as body movement is dependent on a number of variables and the fact that humans are unable to replicate exact same body movement repeatedly.

After thorough testing of the TENG device 10 in position 1 (chest) according to one embodiment, the TENG device 10 was tested with different body motion in position 2 (wrist, as shown in FIG. 3J). The response of the TENG device 10 due to body movement in the wrist is depending on two axis movement of not only flexor retinaculum and flexor digitorum profound but also flexor carpi radialis, flexor carpi ulnaris, and flexor digitorum superficials. Finger opening and closing response as shown in FIGS. 3C and 3E of the nanogenerator device 10 is a result of voluntary and involuntary action of the human body tissues mentioned above. Contraction of thumb makes flexor digitorum superficial tissue contracted as it pushes flexor retinaculum upwards hence it pushes the nanogenerator device 10 outwards. But the inability to compensate for the outward push of the TENG device 10 by moving away from its original position, the TENG device 10 begins contraction, which causes the triboelectric layers 12 and 14 to approach each other and initiates triboelectric voltage generation (~0.3V).

Contraction of thumb followed by the contraction of the index finger is triggered by contraction and expansion of index tendon of extensor digitorum. This contraction and expansion pushes flexor retinaculum, which already have been pushed outward due to the contraction of thumb. Movement of flexor retinaculum does a similar action that has been described with reference to FIGS. 2C and 2D. The generated voltage due to the action of contraction of index finger reaches up to 0.5V. Contraction of index finger action is followed by contraction of middle, ring and small finger which causes contraction of palmaris longus, flexor carpi radials and flexor carpi ulnaris subsequently. These contractions generate voltages of 0.5V, 0.1V and 0.7V sequentially.

Also noticeable is the movement of ring finger decreasing the voltage and then increasing again because of cortical neurons that move the ring finger coupled to the small finger. Hence, the central nervous system is unable to distinguish between ring and small finger movement. The extension of the ring finger's ulnar nerve and contraction of radial nerve requires relaxation following by tension. This condition makes the reduction of voltage following by increase during the ring finger movement. The opposite movement initiates a decrease in voltage as extensor retinaculum and flexor retinaculum imitates relaxation following by the relaxation of ulnar nerves and contraction of radial nerveshich relaxes the nanogenerator device 10 from a previously stressed condition.

However, it can be easily inferred from the relaxation cycle shown FIGS. 3C and 3E that relaxation of the ring finger and small finger greatly differs from any other movement due to cortical neurons control from the central nervous system. FIGS. 3C and 3E show a symmetrical response to every single finger movement. This reproducible data demonstrates the nanogenerator device 10 as a very sensitive body motion sensor. The nervous contraction and relaxation of all fingers is repeated in simultaneous motion through wrist opening and closing. The electrical response of wrist opening (simultaneous five Ulnaris relaxation, as shown in FIGS. 3F and 3H) reached equivalent voltage (−3V to +5V) of accumulated response of finger closing or opening (see FIGS. 3c and 3e) one after another.

Response in FIGS. 3f and 3h shows small deflection from ideal smooth response due to cortical neurons and accumulated response of 18 different muscles including flexor pollicis longus, flexor digitorum profoundus, and flexor digitorum superficialis. The response for wrist opening and closing was found as sinusoidal shape which resembles continuous motion generated response. The response of the sensor in position 2 (wrist as shown in FIG. 3J) was further tested by casual body movement, such as "high 5" and handshake of a subject. Response of "high 5" is demonstrated in FIGS. 3H and 3I (enlarged response). The response is owing to not limited to the contraction and relaxation of triceps brachii, brachioradialis, and brachioradialis with radialis muscle's contraction on flexor retinaculum which partially transfer the contraction stresses to the nanogenerator device 10. This stress moves triboelectric layers 12 and 14 towards and away from each other which results in the identical response on each "high 5". This response reached from −3V to +5V during testing according to one embodiment of TENG device 10.

Figure 6:
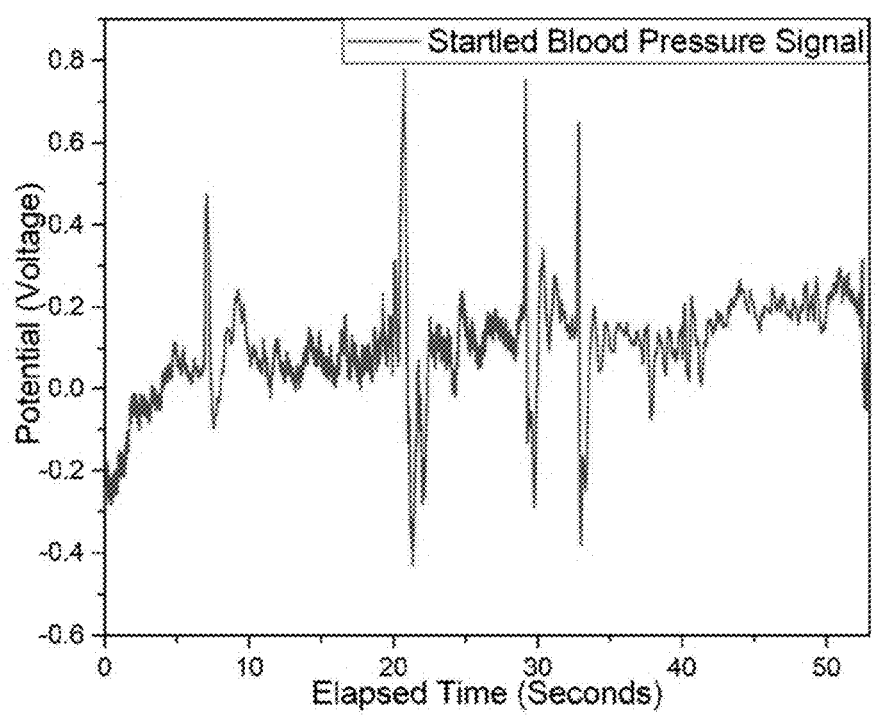
FIG. 6 depicts an electrical signal of startled blood pressure from a TUHMD device having a TENG device therein and placed in the wrist of an individual in accordance with an illustrative embodiment.

During testing of TENG device 10 according to one embodiment, a subject was also tested with sudden shock with startling by external sound and body posture (see FIG. 6) while keeping the TENG device 10 attached to position 2 (as shown in FIG. 3J). The subject showed tremendous blood pressure through his arteries in the wrist which exemplified the triboelectric response. These responses are the peaks that are shown in FIG. 6. After a few different methods of startling the subject, as the brain started to get accustomed to the startling, the blood pressure was not fluctuating. This ensured no peaks after 33 s.

By following these studies, it can be easily inferred that the fabricated nanogenerator device 10 of the present invention according to one embodiment shows a high degree of sensitivity and can easily be used in everyday life for body movement sensory application. Any response created by the TENG device 10 can be analyzed by comparing previously recorded identical responses and generating data of human body motion henceforward burnt calories or any similar value that can be achieved with logged user's Body Mass Index (BMI).

The TENG sensor device 10 according to one embodiment may also have the potential to be used as a sleep monitoring system as it can analyze blood pressure fluctuation and any sudden movement. Both of these data can be recorded and analyzed by computer aided system to generate sleep data (e.g. sleep hour, dreaming etc.). Prolonged data can generate how blood pressure is changing in a longer period of time. This change can give a brief idea about stroke and coronary heart disease conditions. Thus, by utilizing this method in connection with TENG device 10, millions of lives can be saved.

In addition, the ability of the TENG device 10 to work as a vocal sensor has been tested with the TENG device 10 being stuck on the epidermis next to the throat of an individual. As voiceless or voice sounds are affected by the vibrations of the larynx, the device was placed next to the vocal cord to absorb most of the vibration energy. The copper electrode and epidermis were only two things between the vibration of the larynx and the triboelectric layers 12 and 14 to reach the energy from the source to the TENG sensor device 10. During testing of TENG device 10 according to one embodiment, a subject made four attempts of making the sound of the letters "A, B, C, U, T, R, G, V, P, E, R, L". The response of the sound is represented in FIGS. 7A to 7E. The first two responses (attempts 1 and 2) in FIGS. 7B and 7C and the last two responses (attempts 2 and 3) in FIGS. 7D and 7E are recorded with completely opposite reverse electrical polarity connection as shown in FIGS. 7G and 7H. Human voice vibratory energy level cannot be controlled very precisely, hence the shape of the response will be considered as the primary matter of study in this part.

In any event, because of the high level of sensitivity of the TENG device 10, it showed a very good symmetrical response during the identical polarized response in paired attempts (attempts 1 and 2, attempts 3 and 4 of FIG. 7). The vibration caused by the subject is transferred from the vocal cord to thyroid cartilage to epidermis to the TENG device 10. As voice sound is dependent on larynx, tongue, lingual tonsil as well as the esophagus, the TENG device 10 exhibited an excellent combined response from the larynx vibration. This splendid response continued during the response of voiceless sounds.

The larynx covered by Thyroid Cartilage acted as a barrier between the vibration from the larynx and the sensor. However, the rings of thyroid cartilage acted as symmetrical sound amplifier, which nullified the effect of loss of vibrating energy absorbed by the body filters like epidermis and junction between the electrode and the triboelectric layer 12/14.

In this experiment, paper (of layer 12) showed higher peaks in voiceless sounds when placed next to vocal cords. In voiceless sounds (A, E, U) PDMS/PTFE (of layer 14) next to larynx showed the higher responses compared to paper (or layer 12) next to the larynx because the vibration carried out from vowel quadrangle is transmitted through the larynx and shifted towards the TENG device 10 with much broader frequency compared to other sounds. However, voice sounds (B, C, T, R, G, V) made a very identical response on both polarized conditions due to higher amounts of larynx vibration. Response of the voiceless sound of A is identical on both paired responses. This similarity is carried away for almost all the responses. However, the response largely depended on the previous voices as the vibration energy from the last sound is carried away for a few seconds. This created small fluctuation in the response of R. This response is also due to the part of the vibration absorbed by inferior turbinate as the vibration is generated by tongue and inferior turbinate.

Response during pronunciation of G, V and P showed a higher level of symmetry due to the more energy frequent vibration. Sound E showed flatter because the creation of the sound generates far away from the larynx between soft palate and tongue. Because of the higher amount of mechanical flexibility in the polymer (of layer 14), polymer closer to vocal cord (larynx) is well responded through higher peaks during voice sounds. This also produced a higher voltage compared to the lesser mechanically flexible paper (of layer 12) next to the larynx. The response from both polarizations showed an excellent representation of sound response. This phenomenon continued until further experiments.

However, this represented that the sound response is largely dependent on how triboelectric layers 12 and 14 are placed to sound source. These pair of materials (of layers 12 and 14) in the TENG device 10 according to one embodiment showed an extraordinary answer to the current generation of costly sound sensor devices.

Figure 8A:
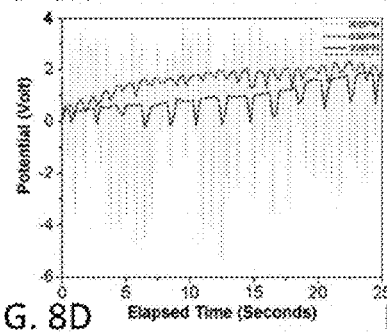
FIG. 8A depicts a comparative performance (Potential Vs Time) of a TUHMD device having a TENG device therein as a power source in 30, 60 and 90 beats per minute (BPM) in accordance with an illustrative embodiment.
Figure 8B:
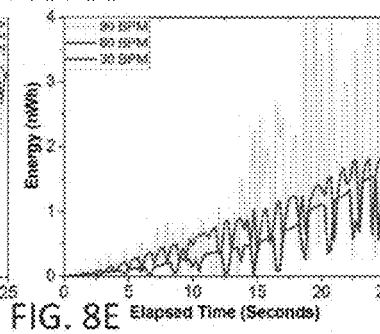
FIG. 8B depicts a comparative performance (Energy Vs Time) of a TUHMD device having a TENG device therein as a power source in 30, 60 and 90 BPM in accordance with an illustrative embodiment.
Figure 8C:
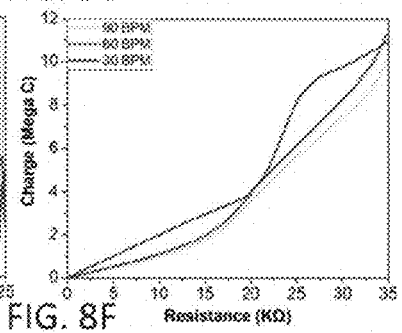
FIG. 8C depicts a comparative performance (Charge Vs Time) of a TUHMD device having a TENG device therein as a capacitor in 30, 60 and 90 BPM in accordance with an illustrative embodiment.
Figure 8D:
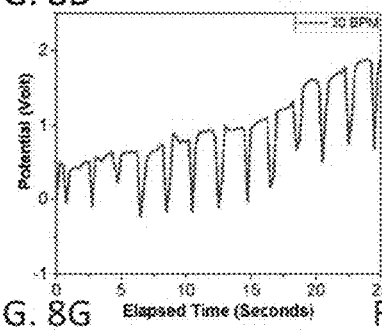
FIG. 8D depicts a voltage response of a TUHMD device having a TENG device therein in 30 BPM in accordance with an illustrative embodiment.
Figure 8E:
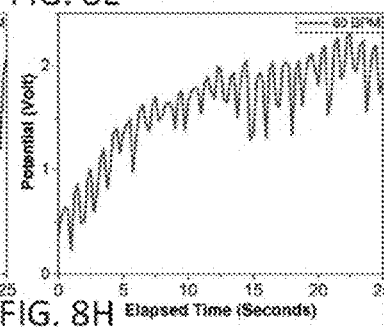
FIG. 8E depicts a voltage response of a TUHMD device having a TENG device therein in 60 BPM in accordance with an illustrative embodiment.
Figure 8F:
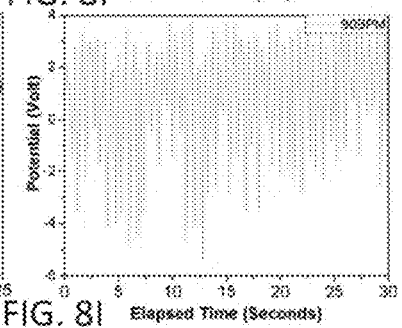
FIG. 8F depicts a voltage response of a TUHMD device having a TENG device therein in 90 BPM in accordance with an illustrative embodiment.
Figure 8G:
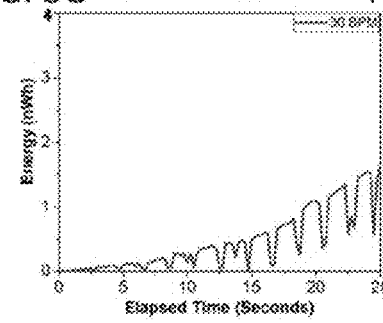
FIG. 8G depicts an energy response of a TUHMD device having a TENG device therein in 30 BPM in accordance with an illustrative embodiment.
Figure 8H:
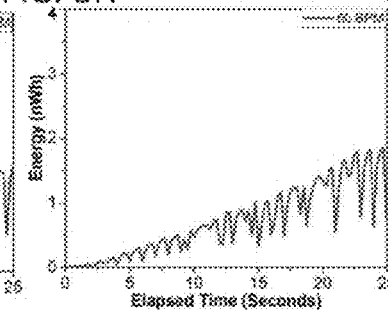
FIG. 8H depicts an energy response of a TUHMD device having a TENG device therein in 60 BPM in accordance with an illustrative embodiment.
Figure 8I:
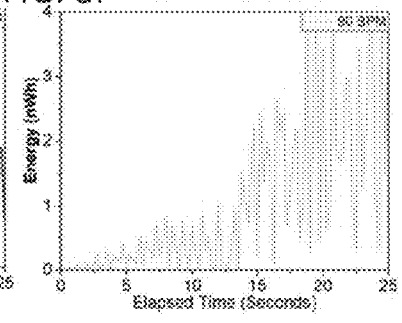
FIG. 8I depicts an energy response of a TUHMD device having a TENG device therein in 90 BPM in accordance with an illustrative embodiment.

Proficiency of TUHMD 100 (incorporating TENG device 10) as a probable power source has been tested with applied minimal stress at different beats per minute (BPM). FIG. 8A demonstrates the comparative voltage production of the device with different load frequency (30 BPM, 60 BPM, 90 BPM). It can be easily inferred from the data that the amount of voltage production can be increased with the amount of applied stresses. From FIGS. 8D, 8E and 8F, it is easily deductible that the value of voltage produced during different frequencies shows different characteristics. FIGS. 9A, 9B, and 9C reveal the highest potential that has been reached for 30 BPM, 60 BPM and 90 BPM is 4.5V, 5V, and 6V respectively after 100 seconds of operation during testing of TENG device 10 in accordance with one embodiment of the present invention.

Lower stress frequency contributes smoother voltage production as the PDMS/PTFE (of layer 14) and Paper (of layer 12) have more time to get closer and return to their original positions hence more possibilities for smoother charge transfer from one surface to another and one electrode to another electrode through the circuit. Higher frequency makes the TENG device 10 more susceptible to charge transfer that has been accumulated in the last cycle of induced stress. As stress frequency intensifies, potential gets more improbable. This similar pattern is visible in FIGS. 8B, 8G, 8H, and 8I where energy is represented with respect to time. More frequent induced stress brings triboelectric layers 12 and 14 closer and away from each other more frequently. Hence charge transfer and energy production become more frequent. This reciprocation action generated the highest 15.5 nWh, 15 nWh and 13 nWh for 30 BPM, 60 BPM, and 90 BPM, respectively which is demonstrated in FIGS. 9D, 9E, and 9F.

The increase in potential with time and applied stress, as shown in FIGS. 8D-8I, verifies the characteristics of the TENG device 10 (and TUHMD 100) as a capacitor. As triboelectric layers 12 and 14 have stayed as close to each other with a small gap between them, this turns the TENG device 10 (and TUHMD 100) into a capacitor. Accumulated charge from the previous cycle continues to the next cycle. Hereafter, the TENG device 10 shows higher charge on every single cycle compared to the previous cycle.

However, this deflects from original characteristics in 90 BPM (see FIGS. 8F and 8I) stress frequency as triboelectric layers move faster and produced charge has lesser time to get accumulated and released. Because of higher conductivity, the release becomes higher compared to charge accumulation. This characteristic also affects charge accumulation as higher stress frequency shows smoother charge vs. resistance than lower frequency. Because of higher number of short circuits in higher frequency, the device starts getting more opportunity to release charge and it reflects a lesser accumulated charge.

Due to the same reason, the lower frequency demonstrates more charge vs resistance and steeper results. Though accumulated charge and voltage differ from stress frequencies, it is evident that the ability of TENG device 10 as nanogenerator in terms of energy generation is not very much affected by how frequent the TENG device 10 (of TUHMD 100) is stressed. Therefore, it can be boldly said that a fabricated TUHMD 100 (incorporating TENG device 10 of the present invention) can be used as a power source in any load conditions according to certain embodiments of the present invention.

Most wearable devices relying on an external power source can only run for so long on a charge before having to be recharged. For example, smart watches from Apple, Inc. can run up to 18 hours with a single charge. Smartwatches from Fitbit, Inc. can run for 4+ days, Garmin Forerunner may last 11+ days, while Samsung Galaxy watch can run up to 3 days with a single charge. This clearly shows the limitation of the current and latest smart devices. Some companies have come up with different ways of overcoming this power limitation. For example, Matrix Industries came out with a smartwatch with pyroelectric materials that requires zero charging requirements. MMT has initiated integration of solar cell into a smartwatch such that the smartwatch will not need to be plugged in to get recharged. Other corporations have initiated a battery-pyroelectric hybrid system for enhancing the battery life. However, these integrations are expensive to manufacture and have resulted as a more costly burden to the consumers.

All the initiatives mentioned above are only focused to the powering unit of smart systems alone. But note that this whole charging problem can be solved by thorough integration of sensors into the smart devices wherein the sensors can be used both as sensors and powering units. It is also necessary to bring down the price of costly sensors by utilizing economical materials so that whole price can be reachable to more consumers. This real-time self-powered biomedical monitoring system can be achieved by utilizing the fabricated sensor in combination with nanogenerator (TENG device 10) within TUHMD 100 as has been described herein.

During the nanogenerator application, the TENG device 10 of the present invention may be configured with multi-layered triboelectric layers 12 and 14 to provide the potential of generating up to 1 Wh of energy, which can be utilized to power any kind of health monitoring device (i.e., TUHMD 100) while sensing the change in the body onto which the TUHMD device 100 is attached.

Figure 10A:
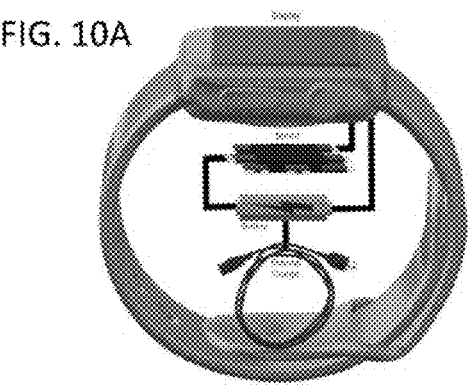
FIG. 10A depicts a conventional electrical system (simplified) in a conventional smartwatch in accordance with an illustrative embodiment.
Figure 10B:
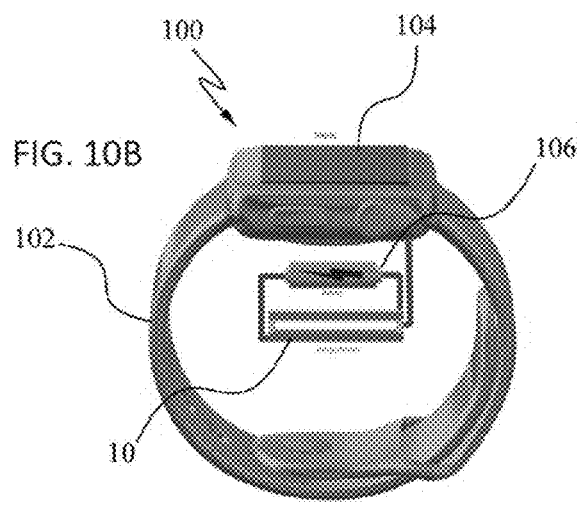
FIG. 10B depicts a proposed electrical system in a wearable TUHMD device configured as a smartwatch in accordance with an illustrative embodiment.
Figure 10C:
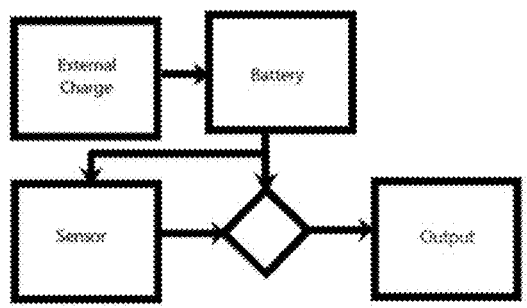
FIG. 10C depicts a system flowchart of the conventional smartwatch device of FIG. 10A in accordance with an illustrative embodiment.
Figure 10D:
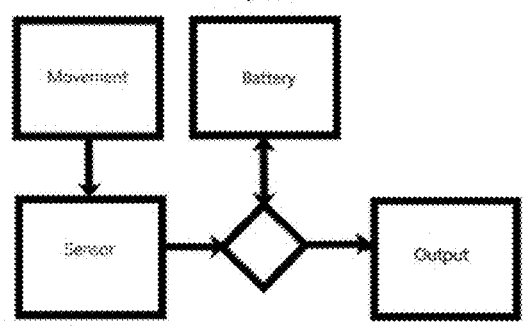
FIG. 10D depicts a system flowchart of the wearable TUHMD device configured as a smartwatch system of FIG. 10B in accordance with an illustrative embodiment.

As an example, a current smart device that has been charging a Li-ion battery by utilizing external charging sources is illustrated schematically in FIG. 10A. The current conventional simplified electrical system for such a smart device is represented in FIG. 10C. As shown, the charging system uses external power sources to store energy into a rechargeable battery. This stored energy is used to power sensors, system as well as output (e.g. display). This whole system can be upgraded as shown in FIGS. 10B and 10D to create a TUHMD device 100 in accordance with one embodiment of the present invention. As shown in FIGS. 10B and 10D, the TUHMD device and system 100, the battery of the smart device 100 may receive charge from the triboelectric sensor/nanogenerator (TENG) device 10 incorporated therein. This sensor 10 will be scavenging energy from the human body motion while sensing its power source characteristics. This charged power is used through the whole system 100 including powering the output.

Figure 10E:
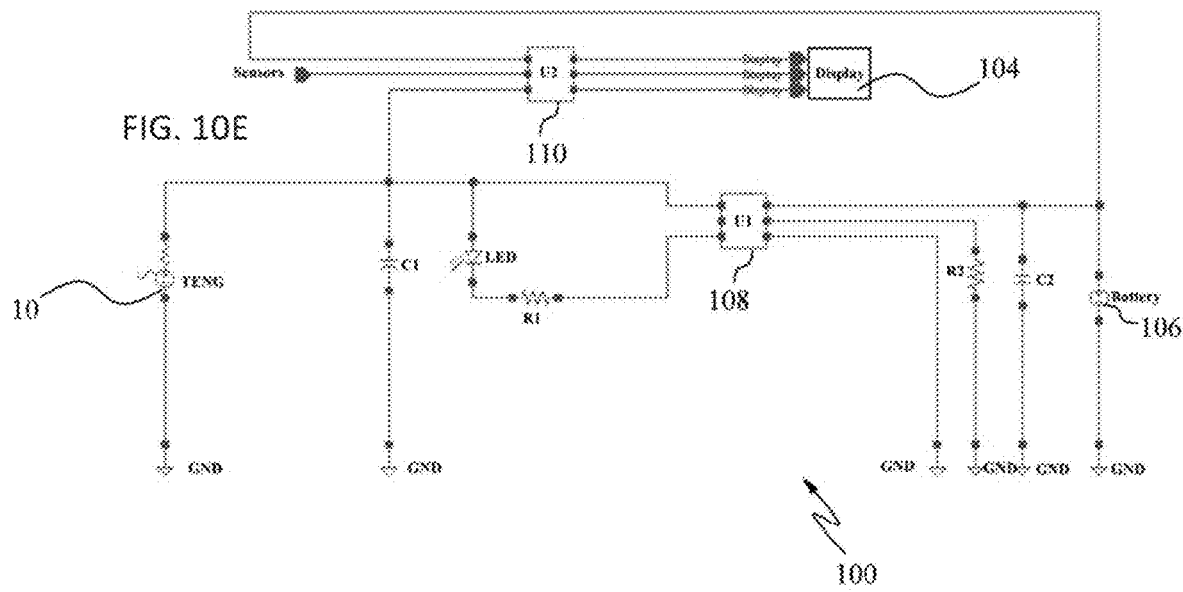
FIG. 10E depicts a representative simplified circuitry connection for the wearable TUHMD device configured as a smartwatch system of FIG. 10B in accordance with an illustrative embodiment.

A simplified electrical circuit for the TUHMD device and system 100 of the present invention is shown in FIG. 10E in accordance with one embodiment of the present invention. In this circuitry representation, the sensor is represented as TENG 10, short for triboelectric nanogenerator/sensor. This is powering two unit systems: U1 and U2. The U1 unit system is responsible for charging the device 100 and the U2 unit system is responsible for sensory signal processing which will receive signal from other sensors (e.g. accelerometer, gyroscope) and represent to the user through output units. From the TENG device 10 incorporated therein, the power will be sent to U2 unit system for sensory actions as well the power will be sent to the battery through an LED for notification of charging.

The UI unit system is charging the battery with ample amount of grounded (GND) connection for better safety of the circuit. Capacitors C1 and C2 are used to smooth the whole operation. This whole simplified circuitry system of TUHMD 100 can be a viable solution for current costly repetitive smart watch charging system which usually charges around $15 to $55 per device. Thus, this big financial charge can be reduced to less than $1 per device using PTEFE/PDMS copolymer (in layer 14 of TENG 10) with readily available paper (of layer 12 of TENG 10). This small change has the potential to make a large change in user level as well as bringing smart devices closer to more people. As a requirement of the charging devices can be lowered in an enormous amount, the number of end users will be increased with the number of satisfied customers due to the lesser amount of repetitive charging cycles.

In some embodiments of the present invention, the TUHMD device and system 100 may comprise a universal cost effective, self-powered highly sensitive health monitoring device with the capability of detecting human body motion and converting same to electrical energy. Because of inexpensive materials and simple structure, the device 100 may be suitable for mass production and a consumer oriented electronic market. Identical signals detectable at virtually any body skin surface render the device 100 competitive with current body motion sensor but with the added advantage of eliminating the necessity for charging the wearable electronics and eliminating the requirement for recharging the device 100. Under applied stresses on any axis, the TENG device 10 has the ability to operate smoothly and power any small-scale wearable electronics (including but not limited to TUHMD 100 of the present invention) as well as any large-scale application with voltage production range up to 12V. The inclusion of the TENG device 10 to the smartwatch may remove the necessity of periodical recharging systems.

According to one embodiment of the present invention, as shown schematically in FIGS. 10B, 10D and 10E, TUHMD device 100 may be configured as a wearable health monitoring device. TUHMD device 100 may include a band or other component 102 for securing the TUHMD device 100 to a user, a display component 104 for displaying data and information to a user, and a battery component 106 for providing power to TUHMD device 100. As further shown in FIGS. 10B, 10D and 10E, TUHMD device 100 may include a TENG sensor device 10 as described herein, including one or more sets of triboelectric layers 12 and 14 and configured with the capability to detect human body motion and convert it to electrical energy. TUHMD device 100 may further include a first powering unit system (U1) 108 configured for charging the device 100, and a second powering unit system (U2) 110 configured for sensory signal processing, which can receive signal from other sensors (e.g. accelerometer, gyroscope) and represent to the user through output units.

The TUHMD device 100 can reduce the cost of health monitoring systems and increase consumer satisfaction. The potential to save human lives that require uninterrupted monitoring of the human body causes the device 100 to have a significant impact on the health care sector. This incorporation will result in huge positive impact on the health sector.

Figure 11:
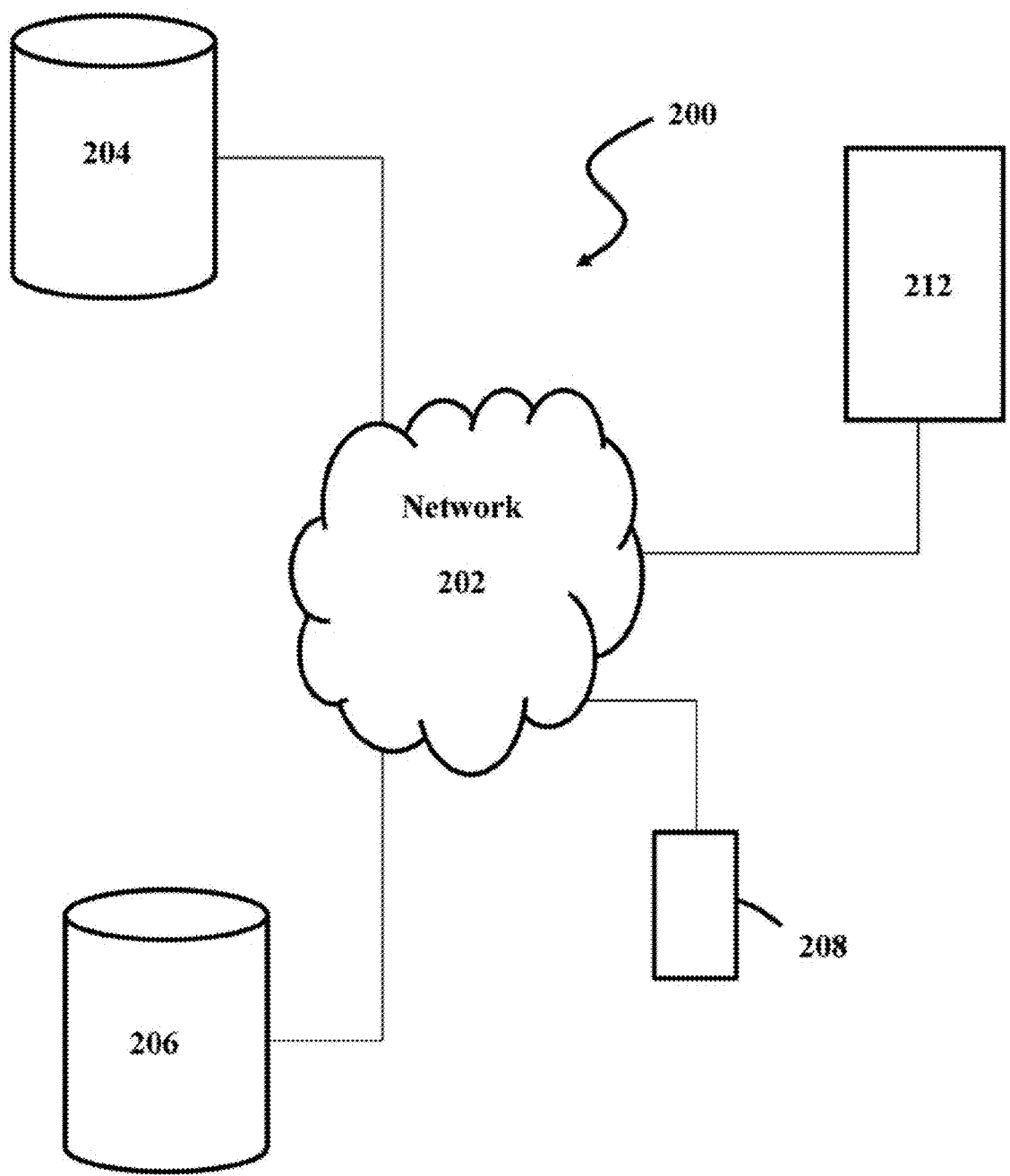
FIG. 11 depicts a schematic representation of a network data processing system that may be configured for use with a wearable TUHMD device system in accordance with an illustrative embodiment.

With reference now to FIG. 11, a schematic representation of a network of data processing systems is depicted in which illustrative embodiments may be implemented. Network data processing system 200 is a network of computing systems in which the illustrative embodiments of TUHMD 100 may be implemented. Network data processing system 200 contains network 202, which is the medium used to provide communications links between various devices (such as TUHMD 100) and computers connected together within network data processing system 200. Network 202 may include connections, such as wire, wireless communication links, or fiber optic cables.

In the depicted example of FIG. 11, network data processing system 200 includes server 204, server 206, wearable device 208 (which may be configured as TUHMD 100 as described herein) and mobile device 212 interconnected through network 202. In this case, network 202 may be the Internet and thus represents a worldwide collection of networks and gateways that use the Transmission Control Protocol/Internet Protocol (TCP/IP) suite of protocols to communicate with one another. Network 202 may also be implemented using a number of different types of networks. For example, network 202 can be comprised of at least one of the Internet, an intranet, a local area network (LAN), a metropolitan area network (MAN), or a wide area network (WAN).

Since wearable device 208 (which may be configured as TUHMD 100 as described herein) and mobile device 212 connect to network 202 in which network 202 is the communications media for these network devices, wearable device 208 and mobile device 212 may form an Internet of things (IoT) in which these physical devices can connect to network 202 and exchange information with each other over network 202.

Note further that server 204 and server 206 may represent healthcare providers to which wearable device 208 may be sending real-time health monitoring data.

FIG. 11 is intended as an example, and not as an architectural limitation. As an example, there may be a plurality of wearable devices 208, wherein each wearable device 208 may be used for a different purpose (e.g., a heart rate monitor, a blood pressure monitor, a body temperature monitor, etc.) in FIG. 11. FIG. 11 may also include a plurality of mobile devices 212 (i.e., a mobile phone, a tablet etc.) as well as more servers, some client computer systems etc. Thus, FIG. 11 is used solely for illustrative purposes.

Figure 12:
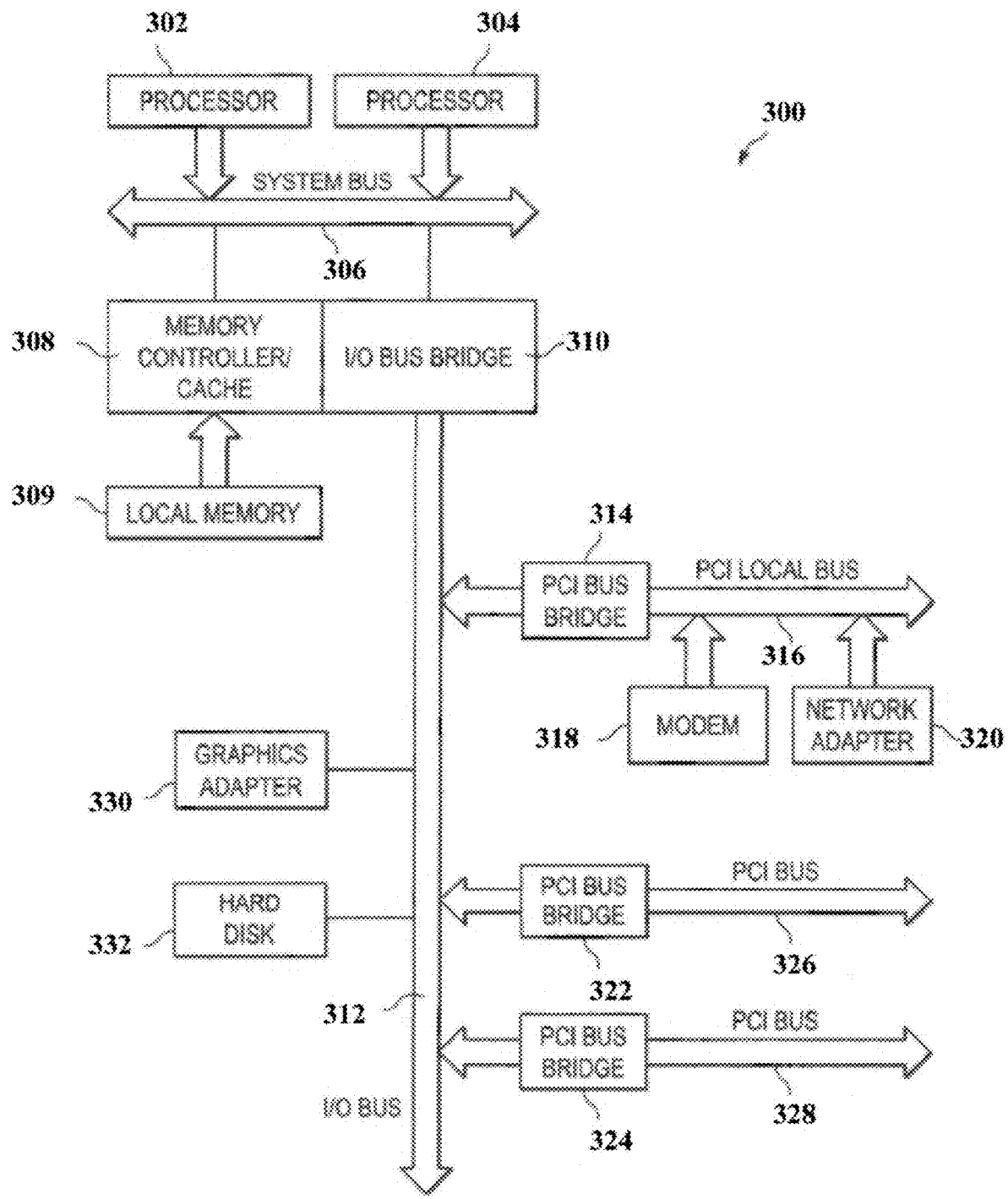
FIG. 12 depicts a schematic representation of a data processing system that may be utilized in connection with the network processing system of FIG. 12 and a wearable TUHMD device system in accordance with an illustrative embodiment.

Turning now to FIG. 12, a block diagram of a data processing system is depicted in accordance with an illustrative embodiment. Data processing system 300 may be used to implement either or both server computer 204 and server computer 206 in FIG. 11. Data processing system 200 may be a symmetric multiprocessor (SMP) system including a plurality of processors, including processor 302 and processor 304 connected to system bus 306. Alternatively, more than one or a single processor system may be employed. Also connected to system bus 306 is memory controller/cache 308, which provides an interface to local memory 309. I/O bus bridge 310 is connected to system bus 306 and provides an interface to I/O bus 312. Memory controller/cache 308 and I/O bus bridge 310 may be integrated as depicted.

Peripheral component interconnect (PCI) bus bridge 314, connected to I/O bus 312, provides an interface to PCI local bus 316. A number of modems may be connected to PCI local bus 316. Typical PCI bus implementations will support four PCI expansion slots or add-in connectors. Communications links to server 204, shown in FIG. 11, or to other computer systems (not shown) in FIG. 11 may be provided through modem 318 and network adapter 320 connected to PCI local bus 316 through add-in boards.

Additional PCI bus bridges, such as PCI bus bridge 322 and PCI bus bridge 324, provide interfaces for additional PCI local bus 326 and PCI local bus 328, from which additional modems or network adapters may be supported. In this manner, data processing system 300 allows for connections to multiple computer systems. A memory-mapped graphics adapter 330 and hard disk 332 may also be connected to I/O bus 312 as depicted, either directly or indirectly.

Those of ordinary skill in the art will appreciate that the hardware depicted in FIG. 12 may vary. For example, other peripheral devices, such as optical disk drives, universal serial bus (USB) drives and the like, also may be used, in addition to or in place of, the hardware depicted. Thus, the depicted example is not meant to imply architectural limitations.

Note that, some of the functional units that will be described in this disclosure are labeled as modules in order to more particularly emphasize their implementation independence. For example, a module may be implemented as a hardware circuit comprising custom very large scale integration (VLSI) circuits or gate arrays, off-the-shelf semiconductors such as logic chips, transistors, or other discrete components. A module may also be implemented in programmable hardware devices such as field programmable gate arrays, programmable array logic, programmable logic devices or the like. Further, modules may also be implemented in software for execution by various types of processors.

Figure 13:
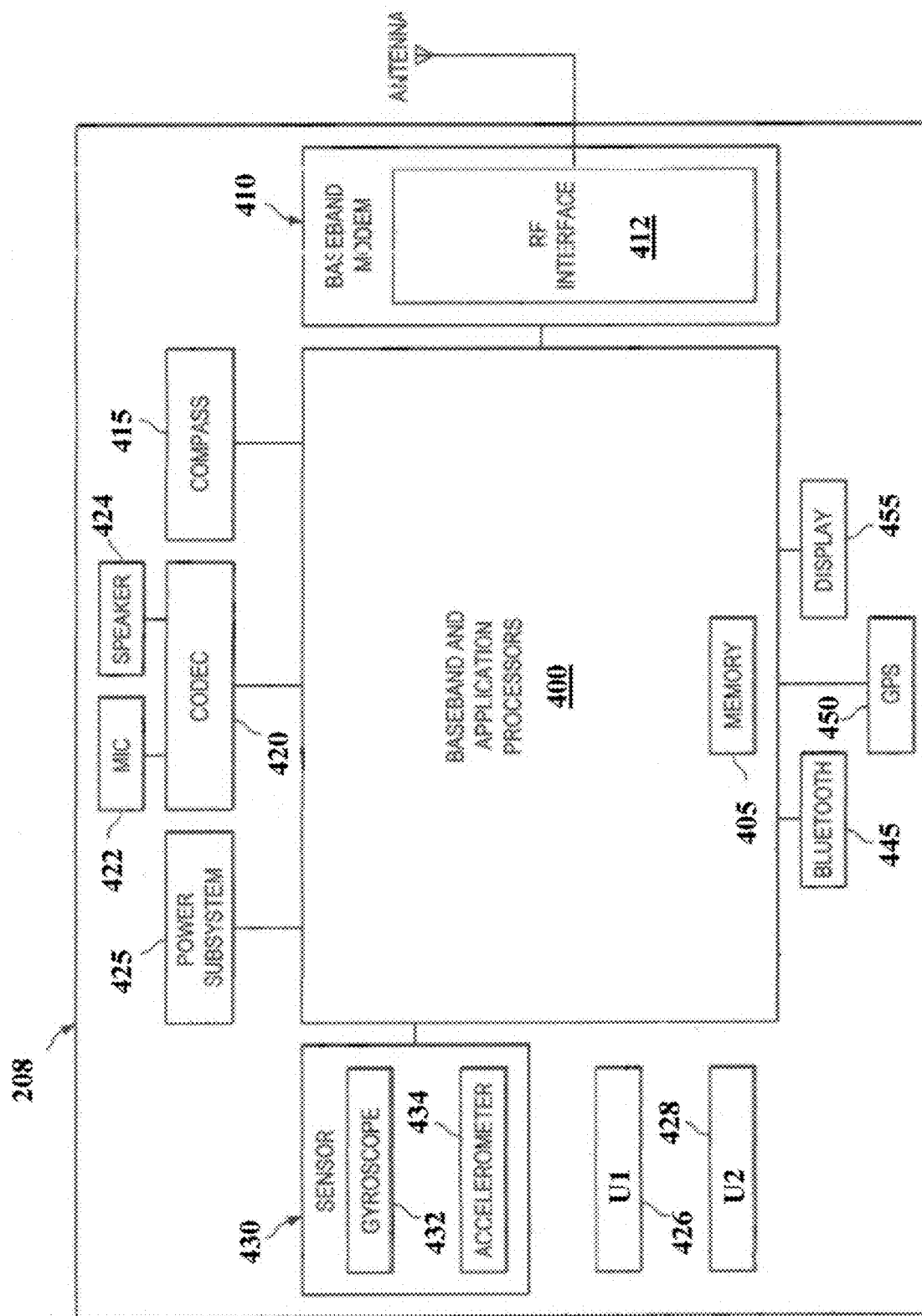
FIG. 13 depicts a schematic representation of a wearable TUHMD device system in accordance with an illustrative embodiment.

FIG. 13 depicts a block diagram of a wearable device 208 of FIG. 11, which may be configured as TUHMD device 100 in accordance with one embodiment of the present invention. As shown, wearable device 208 may include baseband and application processors 400 having a memory module 405 coupled thereto. Further coupled to baseband and application processors 400 is baseband modem 410 for sending and receiving voice communications. Baseband modem 410 may include a radio frequency (RF) interface 412 that may be connected to an antenna. Power subsystem 425 may be configured to power wearable device 408. Specifically, power subsystem 425 may include the circuitry shown in FIG. 10E that includes TENG 10 of the present invention to power unit systems U1 426 and U2 428 (shown as first power unit system (U1) 108 and second power unit system (U2) 110 in FIG. 10E).

Wearable device 208 may also include a compass 415 for detecting in which direction on a map wearable device 208 is facing, and Global Positioning System (GPS) receiver 450 for determining where on the map wearable device 208 is located. Wearable device 208 may further include sensor module 430 which may include accelerometer sensor 434 and gyroscope sensor 432. Accelerometer sensor 434 may be used to measure acceleration in a 3-dimensional coordinate system and gyroscope sensor 432 may be used to measure orientation changes (or angular velocity). The two sensors may be used to determine whether wearable device 208 is tilted and in what direction etc.

As further shown in FIG. 13, wearable device 208 may also include CODEC module 420 having integrated microphone (mic) 422 and speaker 424. Mic 422 and speaker 424 may be used, among other functions, for ultrasonic communications. For Bluetooth communications, wearable device 208 may use Bluetooth module 445.

As used herein, "a number of" when used with reference to items, means one or more items. For example, "a number of different types of networks" is one or more different types of networks.

The phrase "at least one of," when used with a list of items, means different combinations of one or more of the listed items can be used, and only one of each item in the list may be needed. In other words, "at least one" of means any combination of items and number of items may be used from the list, but not all of the items in the list are required. The item can be a particular object, a thing, or a category.

For example, without limitation, "at least one of item A, item B, or item C" may include item A, item A and item B, or item B. This example also may include item A, item B, and item C or item B and item C. Of course, any combinations of these items can be present. In some illustrative examples, "at least one of" can be, for example, without limitation, two of item A; one of item B; and ten of item C; four of item B and seven of item C; or other suitable combinations.

The description of the different illustrative embodiments has been presented for purposes of illustration and description and is not intended to be exhaustive or limited to the embodiments in the form disclosed. The different illustrative examples describe components that perform actions or operations. In an illustrative embodiment, a component may be configured to perform the action or operation described. For example, the component may have a configuration or design for a structure that provides the component an ability to perform the action or operation that is described in the illustrative examples as being performed by the component.

Many modifications and variations will be apparent to those of ordinary skill in the art. Further, different illustrative embodiments may provide different features as compared to other desirable embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

BIBLIOGRAPHY

The following references are incorporated herein in their entirety.
1. Wang, Y., Yang, Y. & Wang, Z. L. *npj Flexible Electronics* 1, 10 (2017).
2. Yang, Y. et al. *ACS Nano* 12, 2027-2034 (2018).
3. Zhang, Q. et al. *Nano Energy* 55, 151-163 (2019).
4. Kang, M., Park, E., Cho, B. H. & Lee, K.-S. *Int Neurourol J* 22, S76-82 (2018).
5. Haghi, M., Thurow, K. & Stoll, R. *Healthc Inform Res* 23, 4-15 (2017).
6. Traverse, C. J., et al. *Nature Energy* 2, 849 (2017).
7. Cuckler, G. A. et al. National Health Expenditure Projections, 2017-26: Despite Uncertainty, Fundamentals Primarily Drive Spending Growth. *Health Affairs* 37, 482-492 (2018).
8. Chowdhury, A. R. et al. *Energy Technology* 0,
9. Chowdhury, A. R. et al. *Nano-Structures & Nano-Objects* (2018).
10. Ma, M. et al. *Nano Res.* 11, 2951-2969 (2018).
11. Ma, M. et al. *Advanced Functional Materials* 25, 6489-6494 (2015).
12. Kaur, N. & Pal, K. *Energy Technology* 6, 958-997 (2018).
13. Rathore, S., Sharma, et al. A Critical Review on Triboelectric Nanogenerator. *IOP Conference Series: Materials Science and Engineering* 377, 012186 (2018).
14. Wu, H., Huang, et al. *Advanced Materials* 28, 9881-9919 (2016).
15. Fan, F.-R. et al. *Nano Lett.* 12, 3109-3114 (2012).
16. Wang, Z. L. *ACS Nano* 7, 9533-9557 (2013).
17. Zhang, X.-S. et al. *Nano Energy* 47, 410-426 (2018).
18. Ning, C. et al. *Journal of Materials Chemistry A* 6, 19143-19150 (2018).
19. Pan et al., Fundamental theories and basic principles of triboelectric effect: A review. Friction, 7, 2-17 (2019).
20. The Triboelectric Series-AlphaLab, Inc. *AlphaLab, Inc.*
21. Ruan, M. et al. *RSC Adv.* 7, 41339-41344 (2017).
22. Sun, D., Li, B.-B. & Xu, Z.-L. *Korean J Chem. Eng.* 30, 2059-2067 (2013).
23. Weng, B., et al. *Cellulose* 22, 1311-1320 (2015).
24. Costa, M. N. et al. *Nanotechnology* 25, 094006 (2014).
25. Sahin, H. T. & Arslan, M. B. *Int J Mol Sci* 9, 78-88 (2008).
26. Fischer, S. C. L. et al. *Journal of the Mechanical Behavior of Biomedical Materials* 61, 87-95 (2016).
27. Majeed, S. et al. *Nanoscale Res Lett* 7, 296 (2012).
28. Yoon, H.-J., Ryu, H. & Kim, S.-W. *Nano Energy* 51, 270-285 (2018).
29. Kim, Y. J. et al. *RSC Adv.* 7, 49368-49373 (2017).
30. MacMahon, S. et al. *The Lancet* 335, 765-774 (1990).
31. Lehrer, S. *Understanding Lung Sounds: Third Edition.* (Steven Lehrer, 2018).
32. U.S. Pat. No. 9,728,176B2
33. Apple Watch Series 4-Design. *Apple*
34. Specifications|Samsung Galaxy Watch. *The Official Samsung Galaxy Site* (Accessed: 26 Feb. 2019)
35. Garmin & subsidiaries, G. L. or its. Forerunner® 235|Running Watch. *Garmin* (Accessed: 26 Feb. 2019)
36. Fitbit Versa™ Smartwatch. (Accessed: 26 Feb. 2019)
37. Matrix PowerWatch. *Matrix PowerWatch* (Accessed: 26 Feb. 2019)
38. MMT—Manufacture Modules Technologies. (Accessed: 26 Feb. 2019)
39. Apple Watch Parts. *iFixit* (Accessed: 26 Feb. 2019)
40. Samsung Smartwatch Parts. *iFixit* (Accessed: 26 Feb. 2019)
41. New Apple Watch Has Lowest Ratio of Hardware Costs to Retail Price, IHS Teardown Reveals—IHS Technology. (Accessed: 26 Feb. 2019)

What is claimed is:

1. A health monitoring device comprising:
a wearable device having a surface suitable for being in contact with a skin surface of a user;
a triboelectric nanogenerator (TENG) positioned on a portion of the surface capable of generating electrical energy from mechanical energy;
a means for transmitting electrical energy generated by the TENG to the device surface in contact with the skin surface;
a means for continuously measuring physiological data, and
a means for transmitting physiological data received at the device surface in contact with the user to a receiver, wherein the physiological data provides for classifying the user as a high disease symptom user or a low disease symptom user as compared to an average non-disease user symptom reference.

2. The health monitoring device of claim 1, wherein the TENG comprises a paper-based material layer.

3. The health monitoring device of claim 2, wherein the paper-based material layer includes a copper film provided thereon.

4. The health monitoring device of claim 2, wherein the TENG further comprises a polymer-based material layer.

5. The health monitoring device of claim 4, wherein the polymer-based material layer includes a copper film provided thereon.

6. The health monitoring device of claim 5, wherein the polymer-based material layer comprises a Polydimethylsiloxane/Polytetrafluoroethylene (PDMS/PTFE) copolymer composite.

7. The health monitoring device of claim 1, wherein the physiological data is transmitted in an uninterrupted stream of data to the receiver.

8. A health monitoring system configured to receive physiological data from one or more users, said system comprising:
a health monitoring device comprising:
a wearable device having a surface suitable for being in contact with a skin surface of a user;
a triboelectric nanogenerator (TENG) positioned on a portion of the surface capable of generating electrical energy from mechanical energy received;
a means for transmitting electrical energy generated by the TENG to the device surface in contact with the skin surface;
a means for continuously measuring physiological data, and a means for transmitting physiological data received at the device surface in contact with the user;

a mobile receiver device configured to receive the transmitted physiological data from said health monitoring device associated with the user, and one or more servers configured to store and/or process the physiological data from said health monitoring device associated with the user, wherein the physiological data is transmitted from the mobile receiver device to the one or more servers by means of a network, wherein the physiological data provides for classifying the user as a high disease symptom user or a low disease symptom user as compared to an average non-disease user symptom reference.

9. The health monitoring system of claim 8, wherein the TENG comprises a paper-based material layer.

10. The health monitoring system of claim 9, wherein the TENG further comprises a polymer-based material layer.

11. The health monitoring system of claim 10, wherein each of paper-based material layer and the polymer-based material layer includes a copper film provided thereon.

12. The health monitoring system of claim 10, wherein the polymer-based material layer comprises a Polydimethylsiloxane/Polytetrafluoroethylene (PDMS/PTFE) copolymer composite.

13. A wearable health monitoring device comprising:
a triboelectric nanogenerator (TENG) configured for contact with a user's skin and capable of generating electrical energy from mechanical energy, said TENG comprising a paper-based material layer and a polymer-based material layer;
a band configured for securing the wearable health monitoring device to the user;
a display screen for displaying information to the user; and
a battery configured for powering the wearable health monitoring device;
wherein the TENG is configured to charge the battery by converting mechanical energy produced by body motion of the user to electrical energy, and
wherein the TENG is further configured as a sensor for collecting physiological information about the user, and
wherein the physiological information about the user provides for classifying the user as a high disease symptom user or a low disease symptom user as compared to an average non-disease user symptom reference.

14. A method for tracking and/or monitoring a subject within a population for disease symptoms associated with a defined disease comprising:
transmitting a simultaneous stream of physiological data from one or more subjects collected from a wearable health monitoring device placed on a skin surface of a subject, said physiological data being transmitted to one or more servers configured to store and/or process the physiological data from said health monitoring device, said wearable device comprising:
a wearable device having a surface suitable for being in contact with a skin surface of a user;
a triboelectric nanogenerator (TENG) positioned on a portion of the surface, capable of generating electrical energy from mechanical energy;
a means for transmitting electrical energy generated by the TENG to the device surface in contact with the skin surface;
a means for continuously measuring physiological data, and
a means for transmitting physiological data received at the device surface in contact with the subject to a designated disease tracking entity; and
transmitting the physiological data from the device to a disease tracking entity by means of a network to the designated disease tracking entity; and
identifying and classifying a subject as a high disease symptom subject or a low disease symptom subject as compared to an average non-disease subject symptom reference,
wherein said classification of the subject provides for the tracking and/or monitoring of the subject.

15. The method of claim 14 wherein the disease tracking entity is a hospital, skilled nursing facility, governmental entity, or population health entity.

16. The method of claim 14 wherein a geographical location of the high disease symptom subjects and the low disease symptom subjects is provided to the disease tracking entity.

17. The method of claim 14 wherein the disease symptoms are associated with a viral disease or a bacterial disease.

18. The method of claim 17 wherein the viral disease is Covid-19.

* * * * *